(12) United States Patent
Valladeau et al.

(10) Patent No.: US 7,034,137 B2
(45) Date of Patent: Apr. 25, 2006

(54) ISOLATED MAMMALIAN MEMBRANE PROTEIN GENES; RELATED REAGENTS

(75) Inventors: Jenny Valladeau, Lyons (FR); Odile Ravel, Lyons (FR); Elizabeth Esther Mary Bates, Lyons (FR); John Ford, Palo Alto, CA (US); Sem Saeland, Lyons (FR); Serge J. E. Lebecque, Civrieux d'Azergue (FR)

(73) Assignee: Schering Corporation, Kenilworth, NJ (US)

( * ) Notice: Subject to any disclaimer, the term of this patent is extended or adjusted under 35 U.S.C. 154(b) by 75 days.

(21) Appl. No.: 10/829,107

(22) Filed: Apr. 21, 2004

(65) Prior Publication Data

US 2004/0192892 A1    Sep. 30, 2004

Related U.S. Application Data

(62) Division of application No. 09/862,802, filed on May 22, 2001, now Pat. No. 6,756,478, which is a division of application No. 09/111,470, filed on Jul. 8, 1998, now Pat. No. 6,277,959.

(60) Provisional application No. 60/053,080, filed on Jul. 9, 1997.

(51) Int. Cl.
  *C07H 21/04* (2006.01)
  *C07H 21/02* (2006.01)

(52) U.S. Cl. .......... 536/23.5; 424/93.2; 424/185.1; 424/192.1; 435/41; 435/69.1; 435/720.1; 530/300; 530/350; 536/23.1

(58) Field of Classification Search .......... 424/93.2, 424/185.1, 192.1; 435/41, 69.1, 720.1; 530/300, 530/350; 536/23.1, 23.5
See application file for complete search history.

(56) References Cited

OTHER PUBLICATIONS

Adams et al., 1997, *GenBank, Accession No. AA380065.*
Caux et al., 1992, *Nature* 360:258-261.
Cella et al., 1997, *Current Opinion in Immunology* 9(1):10-16.
Drickamer 1992, *NATURE* 360:183-186.
Drickamer et al., 1992, *Annu. Rev. Cell Biol* 9:237-264.
Fuhrer et al., 1991, *J. Cell Biology* 114(3):423-431.
Hillier et al., 1997, *GenBank* Accession No. AA4184441.
Hillier et al., 1997, *GenBank* Accession No. AA46401.
Hillier et al., 1997, *GenBank* Accession No. AA677149
Hillier et al., 1995, *GenBank* Accession No. H09206.
Hillier et al., 1995, *GenBank* Accession No. T80687.
Li et al., 1990, *GenBank* Accession No. J05495.
Imai et al., 1995, *Immunology* 86(4):591-598.
Katz et al, 1997, *J. Immunology* 158:5065-5070.
Kawakami et al., 1994, *Jpn. J. Cancer Res.* 85(7):744-749.
Leung et al., 1985, *J. Biol. Chem.* 260(23):12523-12527.
Leung et al., 1995, *GenPept* Accession No. 126133.
Marra et al., 1997, *GenBank* Accession No. AA170532.
Marra et al., 1997, *Gen Bank* Accession No. AA189491.
Marra et al., 1997, *GenBank* Accession No. AA387662.
Marra et al., 1997, *GenBank* Accession No. AA423158.
Marra et al., 1997, *GenBank* Accession No. AA475012.
Marra et al., 1996, *GenBank* Accession No. W33446.
Okubo, 1996 *GenBank* Accession No. C01555.
Ørnotft et al., 1990, *Int. Journal of Cancer* 45:666-672.
Ozaki et al., 1992, *The Journal of Biological Chemistry* 267(13):9229-9235.
Paglia et al., 1996, *Journal of Experimental Medicine* 183 (1):317-322.
Paietta, 1997, *GenBank* Accession No. X55283.
Porgador et al., 1995, *Journal of Experimental Medicine* 182(1):255-260.
Sato et al., 1992, *Journal of Biochemistry* 111(3):331-336.
Spiess, et al., 1994, *GenBank* Accession No. M10058.
Spiess et al., 1994, *GenPept* Accession No. 126132.
Spiess et al., 1994, *GenPetp* Accession No. 126134.
G.F. Springer, 1989, *Molecular Immunology* 26(1):1-5.
Ralph M. Steinman, 1991, *Annual Review of Immunology* 9:271-296.
Ralph M. Steinman, 1996, *Experimental Hematology* 24: 859-869.
Richard J. Stockert, 1995, *Physiological Reviews* 75(3):591-609.
Suzuki et al., 1996, *Journal of Immunology* 156(1):128-135.
Suzuki et al., 1997, *GenBank* Accession No. D50532.
Takezawa et al., 1998, *GenPept* Accession No. 3041697.
Vivier et al., 1997, *Immunology Today* 18(6):286-291.

*Primary Examiner*—Rodney P Swartz

(57) ABSTRACT

Nucleic acids encoding various lymphocyte cell proteins from mammalian, including primate, reagents related thereto, including specific antibodies, and purified proteins are described. Methods of using said reagents and related diagnostic kits are also provided.

10 Claims, No Drawings

ISOLATED MAMMALIAN MEMBRANE PROTEIN GENES; RELATED REAGENTS

This application is a divisional application of U.S. application Ser. No. 09/862,802, filed May 22, 2001, now U.S. Pat. No. 6,756,478, which is a divisional application of U.S. application Ser. No. 09/111,470, filed Jul. 8, 1998, now U.S. Pat. No. 6,277,959, which claims priority from U.S. Provisional Patent Application No. 60/053,080, filed Jul. 9, 1997, all of which are incorporated herein by reference in their entirety.

FIELD OF THE INVENTION

The present invention contemplates compositions related to genes found in lymphocytes, e.g., cells which function in. the immune system. These genes are useful markers, and may function in controlling development, differentiation, and/or physiology of the mammalian immune system. In particular, the application provides nucleic acids, proteins, antibodies, and methods of using them.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.) (1993) *Fundamental Immunology* (3d ed.) Raven Press, N.Y.

Dendritic cells (DC) are antigen-processing or presenting cells, and are found in all tissues of the body. See Steinman (1991) *Annual Review of Immunology* 9:271–296; and Banchereau and Schmitt (eds. 1994) *Dendritic Cells in Fundamental and Clinical Immunology* Plenum Press, NY. These DC can be classified into various categories, including: interstitial dendritic cells of the heart, kidney, gut, and lung; Langerhans cells in the skin and mucous membranes; interdigitating dendritic cells in the thymic medula and secondary lymphoid tissue; and blood and lymph dendritic cells. Although dendritic cells in each of these compartments are CD45+ leukocytes that apparently arise from bone marrow, they may exhibit differences that relate to maturation state and microenvironment.

These dendritic cells efficiently process and present antigens to, e.g., T cells. They stimulate responses from naive and memory T cells in the paracortical area of secondary lymphoid organs. There is some evidence for a role in induction of tolerance.

The primary and secondary B-cell follicles contain follicular dendritic cells that trap and retain intact antigen as immune complexes for long periods of time. These dendritic cells present native antigen to B cells and are likely to be involved in the the affinity maturation of antibodies, the generation of immune memory, and the maintenance of humoral immune responses.

Monocytes are phagocytic cells that belong to the mononuclear phagocyte system and reside in the circulation. See Roitt (ed) *Encyclopedia of Immunology* Academic Press, San Diego. These cells originate in the bone marrow and remain only a short time in the marrow compartment once they differentiate. They then enter the circulation and can remain there for a relatively long period of time, e.g., a few days. The monocytes can enter the tissues and body cavities by the process designated diapedesis, where they differentiate into macrophages and possibly into dendritic cells. In an inflammatory response, the number of monocytes in the circulation may double, and many of the increased number of monocytes diapedese to the site of inflammation.

Antigen presentation refers to the cellular events in which a proteinaceous antigen is taken up, processed by antigen presenting cells (APC), and then recognized to initiate an immune response. The most active antigen presenting cells have been characterized as the macrophages, which are direct developmental products from monocytes; dendritic cells; and certain B cells.

Macrophages are found in most tissues and are highly active in internalization of a wide variety of protein antigens and microorganisms. They have a highly developed endocytic activity, and secrete many products important in the initiation of an immune response. For this reason, it is believed that many genes expressed by monocytes or induced by monocyte activation are likely to be important in antigen uptake, processing, presentation, or regulation of the resulting immune response.

However, dendritic cells and monocytes are poorly characterized, both in terms of proteins they express, and many of their functions and mechanisms of action, including their activated states. In particular, the processes and mechanisms related to the initiation of an immune response, including antigen pocessing and presentation, remain unclear. The absence of knowledge about the structural, biological, and physiological properties of these cells limits their understanding. Thus, medical conditions where regulation, development, or physiology of antigen presenting cells is unusual remain unmanageable.

SUMMARY OF THE INVENTION

The present invention is based, in part, upon the discovery of various mammalian Dendritic Cell Membrane Protein (DCMP) genes, exemplified by the specific DCMP1 and DCMP2 embodiments. Distribution data indicates a broader cellular distribution, and structural data suggests some function. The DCMP1 exhibits similarity to a class of lectins and asialoglycoprotein receptors. The DCMP2 embodiments described exhibit significant sequence similarity to a macrophage cell asialoglycoprotein receptor. The invention embraces agonists and antagonists of the gene products, e.g., mutations (muteins) of the natural sequences, fusion proteins, chemical mimetics, antibodies, and other structural or functional analogs. It is also directed to isolated genes encoding proteins of the invention. Various uses of these different protein or nucleic acid composition are also provided.

In particular embodiments, the invention provides a binding compound comprising an antibody binding site which specifically binds to a DCMP1 protein; or a polypeptide selected from: Gly Val Ser Glu Leu Gln Glu His Thr Thr Gln Lys Ala His Leu Gly His Cys Pro His Cys Pro Ser Val Cys Val Pro (residues 118–144 of SEQ ID NO: 4); Gln Val Ala Thr Leu Asn Asn Asn Ala Ser Thr Glu Gly Thr Cys Cys (residues 166–181 of SEQ ID NO: 4); or Trp Lys Pro Gly Gln Pro Asp Asn Trp Gln Gly His Gly Leu Gly (residues 263–277 of SEQ ID NO: 4). In preferred embodiments, in the binding compound, the antibody binding site is: specifically immunoreactive with a protein of SEQ ID NO: 2 or 8; specifically immunoreactive with a protein of residues 118 to 144 of SEQ ID NO: 4; raised against a purified or recombinantly produced human DCMP1 protein; raised against a purified or recombinantly produced human protein comprising sequence of residues 118 to 144 of SEQ ID NO:

4; in a monoclonal antibody, Fab, or F(ab)2; or the binding compound is: detectably labeled; sterile; or in a buffered composition.

The invention embraces methods using those binding compounds, comprising contacting the binding compound with a biological sample comprising an antigen to form a binding compound:antigen complex. In certain embodiments, the biological sample is human, and the binding compound is an antibody. The invention also provides a detection kit comprising such binding compound and: instructional material for the use of such binding compound for the detection; or a compartment providing segregation of the binding compound.

The invention also provides a substantially pure or isolated polypeptide, which specifically binds to such binding compounds. In various embodiments, the polypeptide: comprises at least a fragment of at least 14 amino acid residues from a primate DCMP1 protein; comprises at least 14 amino acids of residues 118 to 144 of SEQ ID NO: 4; is a soluble polypeptide; is detectably labeled; is in a sterile composition; is in a buffered composition; binds to an sialic acid residue; is recombinantly produced, or has a naturally occurring polypeptide sequence.

Nucleic acid embodiments are provided, including a nucleic acid. encoding a polypeptide above, when purified. Often, the nucleic acid: comprises at least 30 nucleotides of the coding portion of SEQ ID NO: 1 or 7; comprises at least 30 nucleotides from nucleotides 608–688 of SEQ ID NO: 3; or comprises at least 30 nucleotides from nucleotides 752–799 of SEQ ID NO: 3, or it may comprise an insert which selectively hybridizes to a nucleic acid encoding a polypeptide defined above. The invention also provides a cell transfected with such a nucleic acid, e.g., which consists of the protein encoding portions of SEQ ID NO: 1, 7, or the appropriate portions of SEQ ID NO: 3.

The invention provides methods using at least one strand of those nucleic acids to form a duplex nucleic acid, comprising a step of contacting such strand to a sample to a complementary strand capable of specifically hybridizing. In preferred embodiments, the method allows detection of the duplex; or allows histological localization of the duplex.

Alternatively, the invention provides methods of using a described binding composition, comprising a step of contacting the binding composition with a sample to form a binding composition:antigen complex. In preferred embodiments, the sample is a biological sample, including a body fluid; the antigen is on a cell; or the antigen is further purified.

The invention further embraces methods using those polypeptides, comprising contacting the polypeptide with a sample to form a binding composition:polypeptide complex. In preferred embodiments, the polypeptide is further purified.

Another method provided is to modulating dendritic cell physiology or function comprising a step of contacting the cell with: a binding composition as described; a DCMP1 protein as described; or a polypeptide as described. The function may also result in initiation or progression of an immune response. Typically, the contacting is in combination with an antigen, including a cell surface, MHC Class I, or MHC Class II antigen.

DETAILED DESCRIPTION

All references cited herein are incorporated herein by reference to the same extent as if each individual publication or patent application was specifically and individually indicated to be incorporated by reference in its entirety for all purposes.

I. General

The present invention provides DNA sequences encoding mammalian proteins expressed on dendritic cells (DC). For a review of dendritic cells, see Steinman (1991) *Annual Review of Immunology* 9:271–296; and Banchereau and Schmitt (eds. 1994) *Dendritic Cells in Fundamental and Clinical Immunology* Plenum Press, NY. These proteins are designated dendritic cell proteins because they are found on these cells and appear to exhibit some specificity in their expression.

Specific primate, e.g., human, embodiments of these proteins are provided below. Rodent, e.g., mouse, counterparts also exist. The descriptions below are directed, for exemplary purposes, to the human DC genes, but are likewise applicable to structurally, e.g., sequence, related embodiments from other sources or mammalian species, including polymorphic or individual variants. These will include, e.g., proteins which exhibit a relatively few changes in sequence, e.g., less than about 5%, and number, e.g., less than 20 residue substitutions, typically less than 15, preferably less than 10, and more preferably less than 5 substitutions, including 4, 3, 2, or 1. These will also include versions which are truncated from full length, as described, and fusion proteins containing substantial segments of these sequences.

II. Definitions

The term "binding composition" refers to molecules that bind with specificity to a these DC proteins, e.g., in an antibody-antigen interaction. Other compounds, e.g., proteins, can also specifically associate with the respective protein. Typically, the specific association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protein with structural modifications, or may be a wholly unrelated molecule, e.g., which has a molecular shape which interacts with the appropriate interacting determinants. The variants may serve as agonists or antagonists of the protein, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:DC protein complex", as used herein, refers to a complex of a binding agent and DC protein. Specific binding of the binding agent means that the binding agent has a specific binding site that recognizes a site on the respective DC protein. For example, antibodies raised to the DC protein and recognizing an epitope on the DC protein are capable of forming an antibody:DC protein complex by specific binding. Typically, the formation of a binding agent:DC protein complex allows the measurement of that DC protein in a mixture of other proteins and biologics. The term "antibody:DC protein complex" refers to a binding agent:DC protein complex in which the binding agent is an antibody. The antibody may be monoclonal, polyclonal or even an antigen binding fragment of an antibody, e.g., including Fv, Fab, or Fab2 fragments.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Both algorithms for sequence comparison and hybridization conditions are described in greater detail below.

An "isolated" nucleic acid is a nucleic acid, e.g., an RNA, DNA, or a mixed polymer, which is substantially separated from other components which naturally accompany it, e.g., proteins and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogeneous composition of molecules, but will, in some embodiments, contain minor heterogeneity. This heterogeneity is typically found at the polymer ends or portions not critical to a desired biological function or activity.

As used herein, the term "DCMP1 protein" shall encompass, when used in a protein context, a protein having amino acid sequences as shown in SEQ ID NO: 2 or 8, or a significant fragment of such a protein. It refers to a polypeptide which interacts with the respective DCMP1 protein specific binding components. These binding components, e.g., antibodies, typically bind to the DCMP1 protein with high affinity, e.g., at least about 100 nM, usually better than about 30 nM, preferably better than about 10 nM, and more preferably at better than about 3 nM.

The term "DCMP2 forms" refers to the sequences provided in SEQ ID NO: 4 and 10. The nucleotide and corresponding amino acid sequence of primate, e.g., human, protein related to lectin/asialoglycoprotein family members, designated DCMP2, isolated from a dendritic cell library are provided in SEQ ID NO: 3 and 4. The long form is as shown, while the short. form lacks the sequence corresponding to residues 118–144. The short form may also differ at nucleotide 1064. This is related to a monocyte form of an ASGPR, differing by an insertion between residues 173 and 174, and at residue 270, see Table 1, and insert of sequence encoding GEE between nucleotides 775–776. Another variant form is described in SEQ ID NO: 9 and 10.

The term "polypeptide" or "protein" as used herein includes a significant fragment or segment of said protein, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids,more preferably at least 28 amino acids, and, in particularly preferred embodiments, at least about 30 or more amino acids, e.g., 35, 40, 45, 50, 60, 70, etc.

Preferred embodiments exhibit a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12. Segments may refer to either peptides or oligonucleotides.

A "recombinant" nucleic acid is typically defined by its structure. It can be a nucleic acid made by generating a sequence comprising fusion of two fragments which are not naturally contiguous to each other, but is meant to exclude products of nature, e.g., naturally occurring mutant forms.

Certain forms are defined by a method of production. In reference to such, e.g., a product made by a process, the process is use of recombinant nucleic acid techniques, e.g., involving human intervention in the nucleotide sequence, typically selection or production.

Thus, the invention encompasses, for example, nucleic acids comprising sequence derived using a synthetic oligonucleotide process, and products made by transforming cells with a non-naturally occurring vector which encodes these proteins. Such is often done to replace a codon with a redundant codon encoding the same or a conservative amino acid, while typically introducing or removing a sequence recognition site, e.g., for a restriction enzyme. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features, e.g., primer segments, may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants. "Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1–3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable physiologically active state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., e.g., CHS (cholesteryl hemisuccinate) or CHAPS (3-([3-cholamidopropyl]dimethyl-ammonio)-1-propane sulfonate), or in a low enough detergent concentration as to avoid significant disruption of structural or physiological properties of the protein.

"Substantially pure" typically means that the protein is isolated from other contaminating proteins, nucleic acids, or other biologicals derived from the original source organism. Purity, or "isolation", may be assayed by standard methods, typically by weight, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Carriers or excipients will often be added, or the formulation may be sterile or comprise buffer components.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1 or 7, or appropriate parts of 3 and 9. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. The measures of comparison for the DCMP1 do not reflect on those comparison measures for the DCMP2 embodiments.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

Counterpart DCMP proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human DCMP1 protein immunogen with the amino acid sequence depicted in SEQ ID NO: 2 or 8 can be selected to obtain antibodies specifically immunoreactive with that DCMP protein and not with other proteins. These antibodies recognize proteins highly similar to the homologous human DCMP1 protein.

III. Nucleic Acids

These DCMP genes are selectively expressed on dendritic cells. The preferred embodiments, as disclosed, will be useful in standard procedures to isolate genes from other species, e.g., warm blooded animals, such as birds and mammals. Cross hybridization will allow isolation of related proteins from individuals, strains, or species. A number of different approaches are available successfully to isolate a suitable nucleic acid clone based upon the information provided herein. Southern blot hybridization studies should identify homologous genes in other species under appropriate hybridization conditions.

Purified protein or defined peptides are useful for generating antibodies by standard methods, as described below. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference. Alternatively, a DCMP antigen binding composition can be useful as a specific binding reagent, and advantage can be taken of its specificity of binding, for, e.g., purification of a DCMP protein.

The specific binding composition can be used for screening an expression library made from a cell line which expresses the respective DCMP protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the antigen.

Table 1: Alignment of primate, e.g., human, lectin/ASGPR family members. ASGPRh1 and ASGPRh2 are hepatic asialoglycoprotein receptors (see SEQ ID NO: 5 and 6); ASGPRm (SEQ ID NO: 12) is a macrophage derived ASGPR; DCMP2 has a sgort (SEQ ID NO: 13), long (SEQ ID NOs: 3 and 4), and variant forms (SEQ ID NOs: 9 and 10), DCMP1 is presented in SEQ ID NO: 2 and 8.

TABLE 1

Alignment of primate, e.g., human, lectin/ASGPR family members.
ASGPRh1 and ASGPRh2 are hepatic asialoglycoprotein receptors
(see SEQ ID NO: 5 and 6); ASGPRm is a macrophage derived ASGPR;
DCMP2 has short, long, and a variant forms, SEQ ID NO: 4 and 10;
DCMP1 is presented in SEQ ID NO: 2 and 8).

```
ASGPRh1    MTKE..YQDLQHLDNEESDHHQLRKGPPPPQPLLQRLCSGP...............RLLLLSLG
ASGPRh2    MAKD..FQDIQQLSSEENDHP.FHQGPPPAQPLAQRLCSMV................CFSLLALS
ASGPRm     MTRT..YENFQYLENKVKVQG.FKNGPLPLQSLLQRLRSGP................CHLLLSLG
DCMP2s     MTRT..YENFQYLENKVKVQG.FKNGPLPLQSLLQRLRSGP................CHLLLSLG
DCMP2l     MTRT..YENFQYLENKVKVQG.FKNGPLPLQSLLQRLRSGP................CHLLLSLG
DCMP2v     MTRT..YENFQYLENKVKVQG.FKNGPLPLQS...................................
DCMP1      MTSEITYAEVR..........FKNEFKSSGINTASSAASKERTAPHKSNTGFPKLLCASLLIFF
feature          ****                                                +++++

ASGPRh1    LSLLLLVVVCVIGS.QNSQLQEELRGLRETFSNFTASTEAQVKGLSTQGGNVGRKMKSLESQLE.
ASGPRh2    FNILLLVVICVTGS.QSAQLQAELRSLKEAFSNFSSSTLTEVQAISTHGGSVGDKITSLGAKLE.
ASGPRm     LGLLLLVIICVVG.FQNSKFQRDLVTLRTDFSNFTSNTVAEIQALTSQGSSLEETIASLKAEVEG
DCMP2s     LGLLLLVIICVVG.FQNSKFQRDLVTLRTDFSNFTSNTVAEIQALTSQGSSLEETIASLKAEVEG
DCMP2l     LGLLLLVIICVVG.FQNSKFQRDLVTLRTDFSNFTSNTVAEIQALTSQGSSLEETIASLKAEVEG
DCMP2v     ..LLLLVIICVVG.FQNSKFQRDLVTLRTDFSNFTSNTVAEIQALTSQGSSLEETIASLKAEVEG
DCMP1      LLLAISFFIAFVIFFQKYS.Q..LLEKKTT.KELVHTTLE....CVKKNNPVEETAWS.......
feature
++++++++

ASGPRh1    .KQQK........................DLSEDHSSLLLHVKQFVSDLRSLSCQMAALQGNGS
ASGPRh2    .KQQQ........................DLKADHDALLFHLKHFPVDLRFVACQMELLHSNGS
ASGPRm     FKQERQA..........................VHSEMLLRVQQLVQDLKKLTCQVATLNNNGE
DCMP2s     FKQERQA..........................VHSEMLLRVQQLVQDLKKLTCQVATLNNN..
DCMP2l     FKQERQAGVSELQEHTTQKAHLGHCPHCPSVCVPVHSEMLLRVQQLVQDLKKLTCQVATLNNN..
DCMP2v     FKQERQA..........................VHSEMLLRVQQLVQDLKKLTCQVATLNNNGE
DCMP1      ..................................................................
feature ASGPRh1    ER....TCCPVNWVEHERSCYWFSRSGKAWADADNYCRLEDAHLVVVTSWEEQKFVQHHIGPVNT
ASGPRh2    QR....TCCPVNWVEHQGSCYWFSHSGKAWAEAEKYCQLENAHLVVINSWEEQKFIVQHTNPFNT
ASGPRm     EASTEGTCCPVNWVEHQDSCYWFSHSGMSWAEAEKYCQLKNAHLVVINSREEQNFVQKYLGSAYT
DCMP2s     .ASTEGTCCPVNWVEHQDSCYWFSHSGMSWAEAEKYCQLKNAHLVVINSREEQNFVQKYLGSAYT
DCMP2l     .ASTEGTCCPVNWVEHQDSCYWFSHSGMSWAEAEKYCQLKNAHLVVINSREEQNFVQKYLGSAYT
DCMP2v     EASTEGTCCPVNWVEHQDSCYWFSHSGMSWAEAEKYCQLKNAHLVVINSREEQNFVQKYLGSAYT
DCMP1      .......CCPKNWKSFSSNCYFISTESASWQDSEKDCARMEAHLLVINTQEEQDFIFQNLQEESA
feature    ..................................................................

ASGPRh1    W.MGLHDQNGP..WKWVDGTDYETGFKNWRPEQPDDWYGHGLGGGEDCA..HFTDDGR...WNDD
ASGPRh2    W.IGLTDSDGS..WKWVDGTDYRHNYKNWAVTQPDNWHGELGGSEDCV..EVQPDGR...WNDD
ASGPRm     W.MGLSDPEGA..WKWVDGTDYATGFQNWKPGQPDDWQGHGLGGGEDCA..HFHPDGR...WNDD
DCMP2s     W.MGLSDPEGA..WKWVDGTDYATGFQNWKPGQPDDWQGHGLGGGEDCA..HFHPDGR...WNDD
DCMP2l     W.MGLSDPEGA..WKWVDGTDYATGFQNWKPGQPDDWQGHGLGGGEDCA..HFHPDGR...WNDD
DCMP2v     W.MGLSDPEGA..WKWVDGTDYATGFQNWKPGQPDDWQGHGLGGGEDCA..HFHPDGR...WNDD
DCMP1      YFVGLSDPEGQRRWQWVDQTPYNESSTFWHPREPSD.......PNERCVVLNFRKSPKRWGWNDV
feature    .............................XXX...............................

ASGPRh1    VCQRPYRWVCETELDKASQEPPLL
ASGPRh2    FCLQVYRWVCEKRRNATGE...VA
ASGPRm     VCQRPYHWVCEAGLGQTSQESH
DCMP2s     VCQRPYHWVCEAGLGQTSQESH
DCMP2l     VCQRPYHWVCEAGLGQTSQESH
DCMP2v     VCQRPYHWVCEAGLGQTSQESH
DCMP1      NCLGPQRSVCEMMKIH.......L
feature    ....................
``` features:
*** internalization domain (an extended domain EITYAEV is seen in the NK receptor NKA);
+++ transmembrane domain;
... C-type lectin domain;
XXX sugar specificity domain.
The DCMP1 receptor is closest in homology to the macrophage lectin in the lectin domain.

Sequence analysis suggests these DCMPs are members of the lectin/asialoglycoprotein superfamily of receptors. The peptide segments can also be used to design and produce appropriate oligonucleotides to screen a library to determine the presence of a similar gene, e.g., an identical or polymorphic variant, or to identify a DC. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding these DC proteins, e.g., subcloning nucleic acid sequences encoding polypeptides into expression vectors, labeling probes, DNA hybridization, and the like are described generally in Sambrook, et al. (1989) *Molecular Cloning—A Laboratory Manual* (2nd ed.) Vol. 1–3, Cold Spring Harbor Laboratory, Cold Spring Harbor Press, NY, which is incorporated herein by reference and hereinafter referred to as "Sambrook, et al." See also, Coligan, et al. (1987 and periodic supplements) *Current Protocols in Molecular Biology* Greene/Wiley, New York, N.Y., referred to as "Coligan, et al."

There are various methods of isolating the DNA sequences encoding these DC proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed with other proteins and selecting specific primers. Such probes can be used directly in hybridization assays to isolate DNA encoding DC proteins, or probes can be designed for use in amplification techniques such as PCR, for the isolation of DNA encoding DC proteins.

To prepare a cDNA library, mRNA is isolated from cells which express the DC protein. cDNA is prepared from the mRNA and ligated into a recombinant vector. The vector is transfected into a recombinant host for propagation, screening and cloning. Methods for making and screening cDNA libraries are well known. See Gubler and Hoffman (1983) *Gene* 25:263–269; Sambrook, et al.; or Coligan, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described, e.g., in Sambrook, et al. or Coligan, et al. Recombinant phage are analyzed by plaque hybridization as described in Benton and Davis (1977) *Science* 196:180–182. Colony hybridization is carried out as generally described in, e.g., Grunstein, et al. (1975) *Proc. Natl. Acad. Sci. USA* 72:3961–3965.

DNA encoding a DC protein can be identified in either cDNA or genomic libraries by its ability to hybridize with the nucleic acid probes described herein, for example in colony or plaque hybridization experiments. The corresponding DNA regions are isolated by standard methods familiar to those of skill in the art. See Sambrook, et al.

Various methods of amplifying target sequences, such as the polymerase chain reaction, can also be used to prepare DNA encoding DC proteins. Polymerase chain reaction (PCR) technology is used to amplify such nucleic acid sequences directly from mRNA, from cDNA, and from genomic libraries or cDNA libraries. The isolated sequences encoding DC proteins may also be used as templates for PCR amplification.

In PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a selected full-length DC protein or to amplify smaller DNA segments as desired. Once such regions are PCR-amplified, they can be sequenced and oligonucleotide probes can be prepared from sequence obtained using standard techniques. These probes can then be used to isolate DNAs encoding other forms of the DC proteins.

Oligonucleotides for use as probes are chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using the chemical degradation method of Maxam and Gilbert in Grossman and Moldave (eds. 1980) *Methods in Enzymology* 65:499–560 Academic Press, New York.

This invention provides isolated DNA or fragments to encode a DC protein, as described. In addition, this invention provides isolated or recombinant DNA which encodes a biologically active protein or polypeptide which is capable of hybridizing under appropriate conditions, e.g., high stringency, with the DNA sequences described herein. Said biologically active protein or polypeptide can be a naturally occurring form, or a recombinant protein or fragment, and have an amino acid sequence as disclosed in SEQ ID NO: 2, 4, 8, or 10. Preferred embodiments will be full length natural isolates, e.g., from a primate. In glycosylated form, the proteins should exhibit larger sizes. Further, this invention encompasses the use of isolated or recombinant DNA, or fragments thereof, which encode proteins which are homologous to each respective DC protein. The isolated DNA can have the respective regulatory sequences in the 5' and 3' flanks, e.g., promoters, enhancers, poly-A addition signals, and others.

IV. Making DC Gene Products

DNAs which encode these DC proteins or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can, e.g., be used to generate polyclonal or monoclonal antibodies; for binding studies; for construction and expression of modified molecules; and for structure/function studies. Each of these DC proteins or their fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired DC gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode the various DC proteins, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a DC protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a DC gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express DC proteins or fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and *Dictyostelium*, may be transformed with DC gene sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the Yip-series), or mini-chromosomes (such as the YCp-series).

Higher eukaryotic tissue culture cells are the preferred host cells for expression of the DC protein. In principle, most any higher eukaryotic tissue culture cell line may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses,. or retroviruses carrying promoters derived, e.g., from such sources as from adenovirus, SV40, parvoviruses, vaccinia virus, or ncytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

In certain instances, the DC proteins need not be glycosylated to elicit biological responses in certain assays. However, it will often be desirable to express a DC polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, a DC gene may be co-transformed with one or more genes encoding mammalian or other glycosylating enzymes. It is further understood that over glycosylation may be detrimental to DC protein biological activity, and that one of skill may perform routine testing to optimize the degree of glycosylation which confers optimal biological activity.

A DC protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985)

Science 230:1003–1008; Brunner, et al. (1991) *J. Cell Biol.* 114:1275–1283; and Coligan, et al. (eds.) (1996 and periodic supplements) *Current Protocols in Protein Science*, John Wiley & Sons, New York, N.Y.

Now that these DC proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. See also Merrified (1986) *Science* 232:341–347; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The DC proteins of this invention can be obtained in varying degrees of purity depending upon the desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and contacting the linked antibodies with solubilized lysates of appropriate source cells, lysates of other cells expressing the protein, or lysates or supernatants of cells producing the proteins as a result of DNA techniques, see below.

Multiple cell lines may be screened for one which expresses said protein at a high level compared with other cells. Various cell lines, e.g., a mouse thymic stromal cell line TA4, is screened and selected for its favorable handling properties. Natural DC cell proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features.

V. Antibodies

Antibodies can be raised to the various DC proteins, including individual, polymorphic, allelic, strain, or species variants, and fragments thereof, both in their naturally occurring (full-length) forms and in their recombinant forms. Additionally, antibodies-can be raised to DC proteins in either their active forms or in their inactive forms. Anti-idiotypic antibodies may also be used.

a. Antibody Production

A number of immunogens may be used to produce antibodies specifically reactive with these DC proteins. Recombinant protein is the preferred immunogen for the production of monoclonal or polyclonal antibodies. Naturally occurring protein may also be used either in pure or impure form. Synthetic peptides made using the human DC protein sequences described herein may also used as an immunogen for the production of antibodies to the DC protein. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the DC protein of interest. When appropriately high titers of antibody to the immunogen are obtained, blood is collected from the animal and antisera are prepared. Further fractionation of the antisera to enrich for antibodies reactive to the protein can be done if desired. See, e.g., Harlow and Lane.

Monoclonal antibodies may be obtained by various techniques familiar to those skilled in the art. Briefly, spleen cells from an animal immunized with a desired antigen are immortalized, commonly by fusion with a myeloma cell. See, e.g., Kohler and Milstein (1976) *Eur. J. Immunol.* 6:511–519, which is incorporated herein by reference. Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Antibodies, including binding fragments and single chain versions, against predetermined fragments of these DC proteins can be raised by immunization of animals with conjugates of the fragments with carrier proteins as described above. Monoclonal antibodies are prepared from cells secreting the desired antibody. These antibodies can be screened for binding to normal or defective DC proteins, or screened for agonistic or antagonistic activity. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen to initiate a humoral immune response. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention can also be used for affinity chromatography in isolating each DC protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby purified DC protein will be released.

The antibodies may also be used to screen expression libraries for particular expression products. Usually the antibodies used in such a procedure will be labeled with a moiety allowing easy detection of presence of antigen by antibody binding.

Antibodies to DC proteins may be used for the analysis or, or identification of specific cell population components which express the respective protein. By assaying the expression products of cells expressing DC proteins it is possible to diagnose disease, e.g., immune-compromised conditions, DC depleted conditions, or overproduction of DC.

Antibodies raised against each DC will also be useful to raise anti-idiotypic antibodies. These will be useful in detecting or diagnosing various immunological conditions related to expression of the respective antigens.

b. Immunoassays

A particular protein can be measured by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of these DC proteins can be performed by a variety of methods known to those skilled in the art. In brief, immunoassays to measure the protein can be competitive or noncompetitive binding assays. In competitive binding assays, the sample to be analyzed competes with a labeled analyte for specific binding sites on a capture agent bound to a solid surface. Preferably the capture agent is an antibody specifically reactive with the DC protein produced as described above. The concentration of labeled analyte bound to the capture agent is inversely proportional to the amount of free analyte present in the sample.

In a competitive binding immunoassay, the DC protein present in the sample competes with labeled protein for binding to a specific binding agent, for example, an antibody specifically reactive with the DC protein. The binding agent may be bound to a solid surface to effect separation of bound labeled protein from the unbound labeled protein. Alternately, the competitive binding assay may be conducted in liquid phase and any of a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the protein.

These DC proteins may also be quantitatively determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of DC proteins in a sample. Electrophoresis is carried out, e.g., on a tissue sample suspected of containing the protein. Following electrophoresis to separate the proteins, and transfer of the proteins to a suitable solid support such as a nitrocellulose filter, the solid support is incubated with an antibody reactive with the denatured protein. This antibody may be labeled, or alternatively may be it may be detected by subsequent incubation with a second labeled antibody that binds the primary antibody.

The immunoassay formats described above employ labeled assay components. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^{3}H$, $^{125}I$, $^{35}S$, $^{14}C$, or $^{32}P$ is used. Non-radioactive labels include ligands which bind to labeled antibodies, fluorophores, chemiluminescent agents, enzymes, and antibodies which can serve as specific binding pair members for a labeled protein. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For reviews of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

A variety of different immunoassay formats, separation techniques, and labels can be also be used similar to those described above for the measurement of specific proteins.

VI. Purified DC Proteins

Primate, e.g., human, DCMP1 nucleotide and amino acid sequences are provided in SEQ ID NO: 1 and 2. Rodent, e.g., mouse, DCMP1 nucleotide and amino acid seqeunces are provided in SEQ ID NO: 7 and 8. Primate, e.g., human, DCMP2 nucleotide and amino acid sequences are provided in SEQ ID NO: 3 and 4. Another variant is described in SEQ ID NO: 9 and 10. Similar primate hepatic asialoglycyprotein sequences are provided in SEQ ID NO: 5 and 6. The peptide sequences allow preparation of peptides to generate antibodies to recognize such segments, and allow preparation of oligonucleotides which encode such sequences.

VII. Physical Variants

This invention also encompasses proteins or peptides having substantial amino acid sequence similarity with an amino acid sequence of a SEQ ID NO: 2 or 8 or selected portions of SEQ ID NO: 4 or 10. Variants exhibiting substitutions, e.g., 20 or fewer, preferably 10 or fewer, and more preferably 5 or fewer substitutions, are also enabled. Where the substitutions are conservative substitutions, the variants will share immunogenic or antigenic similarity or cross-reactivity with a corresponding natural sequence protein. Natural variants include individual, allelic, polymorphic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural allelic and interspecies variations in each respective protein sequence. Typical homologous proteins or peptides will have from 50–100% similarity (if gaps can be introduced), to 75–100% similarity (if conservative substitutions are included) with the amino acid sequence of the relevant DC protein. Identity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif; and the University of Wisconsin Genetics Computer Group (GCG), Madison, Wis.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needlman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Nucleic acids encoding the corresponding mammalian DC proteins will typically hybridize to SEQ ID NO: 1 or 7, or appropriate portion of 3 under stringent conditions. For example, nucleic acids encoding the respective DC proteins will typically hybridize to the nucleic acid of SEQ ID NO: 1, 7, 3, or 9, under stringent hybridization conditions, while providing few false positive hybridization signals. Generally, stringent conditions are selected to be about 10° C. lower than the thermal melting point (Tm) for the sequence being hybridized to at a defined ionic strength and pH. The Tm is the temperature (under defined ionic strength and pH) at which 50% of the target sequence hybridizes to a perfectly matched probe. Typically, stringent conditions will be those in which the salt concentration in wash is about 0.02 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 20–50 mM NaCl at 42° C. Hybridization under stringent conditions should give a background of at least 2-fold over background, preferably at least 3–5 or more.

An isolated DC gene DNA can be readily modified by nucleotide substitutions, nucleotide deletions, nucleotide insertions, and inversions of nucleotide stretches. These modifications result in novel DNA sequences which encode these DC antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant DC protein derivatives include predetermined or site-specific mutations of the respective protein or its fragments. "Mutant DC protein" encompasses a polypeptide otherwise falling within the homology definition of the DC protein as set forth above, but having an amino acid sequence which differs from that of the DC protein as found in nature, whether by way of deletion, substitution, or insertion. In particular, "site specific mutant DC protein" generally includes proteins having significant similarity with a protein having a sequence of SEQ ID NO: 2 or 8. Generally, the variant will share many physicochemical and biological activities, e.g., antigenic or immunogenic, with those sequences, and in preferred embodiments contain most or all of the disclosed sequence. Similar concepts apply to these various DC proteins, particularly those found in various warm blooded animals, e.g., primates and mammals.

Although site specific mutation sites are predetermined, mutants need not be site specific. DC protein mutagenesis can be conducted by making amino acid insertions or deletions. Substitutions, deletions, insertions, or any combinations may be generated to arrive at a final construct. Insertions include amino- or carboxyl-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a respective DC polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, domains or other segments may be"swapped" between different new fusion polypeptides or fragments, typically with related proteins, e.g., withn the lectin or asialoglycoprotein families. Preferably, intact structural domains will be used, e.g., intact Ig portions. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains. Also, alanine scanning mutagenesis may be applied, preferably to residues which structurally are exterior to the secondary structure, which will avoid most of the critical residues which generally disrupt tertiary structure.

"Derivatives" of these DC antigens include amino acid sequence mutants, glycosylation variants, and covalent or aggregate conjugates with other chemical moieties. Covalent derivatives can be prepared by linkage of functionalities to groups which are found in these DC protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents. Also, proteins comprising substitutions are encompassed, which should retain substantial immunogenicity, to produce antibodies which recognize a protein of SEQ ID NO: 2, 4, 8, or 10. Typically, these proteins will contain less than 20 residue substitutions from the disclosed sequence, more typically less than 10 substitutions, preferably less than 5, and more preferably less than three. Alternatively, proteins which begin and end at structural domains will usually retain antigenicity and cross immunogenicity.

A major group of derivatives are covalent conjugates of the DC proteins or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between these DC proteins and other homologous or heterologous proteins are also provided. Heterologous polypeptides may be fusions between different surface markers, resulting in, e.g., a hybrid protein. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of these DC proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a DC protein antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-DC protein antibodies. The DC proteins can also be labeled with a detectable group, e.g., radioiodinated by the chloramine T procedure, covalently bound to rare earth chelates, or conjugated to another fluorescent moiety for use in diagnostic assays. Purification of these DC proteins may be effected by immobilized antibodies.

Isolated DC protein genes will allow transformation of cells lacking expression of a corresponding DC protein, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of these DC proteins. Subcellular fragments, e.g., cytoplasts or membrane fragments, can be isolated and used.

VIII. Binding Agent:DC Protein Complexes

A DC protein that specifically binds to or that is specifically immunoreactive with an antibody generated against a defined immunogen, such as an immunogen consisting of the amino acid sequence of SEQ ID NO: 2, 4, 8, or 10, is determined in an immunoassay. The immunoassay uses a polyclonal antiserum which was raised to the protein of SEQ ID NO: 2, 4, 8, or 10. This antiserum is selected to have low crossreactivity against other members of the related families, and any such crossreactivity is removed by immunoabsorbtion prior to use in the immunoassay.

In order to produce antisera for use in an immunoassay, the protein of SEQ ID NO: 2, 4, 8, or 10, is isolated as described herein. For example, recombinant protein may be produced in a mammalian cell line. An inbred strain of mice such as balb/c is immunized with the appropriate protein using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other related proteins, using a competitive binding immunoassay such as the one described in Harlow and Lane, supra, at pages 570–573. Preferably two different related protiens are used in this determination in conjunction with a given DC protein. For example, with the lectin protein, at least two other family members are used to absorb out shared epitopes. In conjunction with the DCMP1 family member, two other members of the family are used. These other family members can be produced as recombinant proteins and isolated using standard molecular biology and protein chemistry techniques as described herein.

Immunoassays in the competitive binding format can be used for the crossreactivity determinations. For example, the protein of SEQ ID NO: 2 or 8 can be immobilized to a solid support. Proteins added to the assay compete with the binding of the antisera to the immobilized antigen. The ability of the above proteins to compete with the binding of the antisera to the immobilized protein is compared to the protein of SEQ ID NO 2 or 8. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the DC protein of SEQ ID NO: 2 or 8). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 or 8 that is required, then the second protein is said to specifically bind to an antibody generated to the immunogen.

It is understood that DC proteins are likely a family of homologous proteins that comprise two or more genes. For a particular gene product, such as the human Ig family member protein, the invention encompasses not only the amino acid sequences disclosed herein, but also to other proteins that are allelic, polymorphic, non-allelic, or species variants. It also understood that the term "human DC protein" includes nonnatural mutations introduced by deliberate mutation using conventional recombinant technology such as single site mutation, or by excising short sections of DNA encoding these proteins or splice variants from the gene, or by substituting or adding small numbers of new amino acids. Such minor alterations must substantially maintain the immunoidentity of the original molecule and/or its biological activity. Thus, these alterations include proteins that are specifically immunoreactive with a designated naturally occurring respective DC protein, e.g., the human DC protein exhibiting SEQ ID NO: 4. Particular protein modifications considered minor would include conservative substitution of amino acids with similar chemical properties, as described above for each protein family as a whole. By aligning a protein optimally with the protein of SEQ ID NO 2 or 8, and by using the conventional immunoassays described herein to determine immunoidentity, one can determine the protein compositions of the invention.

IX. Uses

The present invention provides reagents which will find use in diagnostic applications as described elsewhere herein, e.g., in the general describoion for developmental abnormalities, or below in the description of kits for diagnosis. In particular, the genes will be useful as markers for distinguishing cell types, including genomic aspects of cells, as well as mRNA and protein expression patterns.

DC genes, e.g., DNA or RNA may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from DC sequences may be used in in situ assays to detect chromosomal abnormalities.

Antibodies and other binding agents directed towards DC proteins or nucleic acids may be used to purify the corresponding DC protein molecule. As described in the Examples below, antibody purification of DC proteins is both possible and practicable. Antibodies and other binding agents may also be used in a diagnostic fashion to determine whether DC components are present in a tissue sample or cell population using well-known techniques described herein. The ability to attach a binding agent to a DC protein provides a means to diagnose disorders associated with expression misregulation. Antibodies and other DC protein binding agents may also be useful as histological or forensic markers. As described in the examples below, the expression of each of these proteins is limited to specific tissue types. By directing a probe, such as an antibody or nucleic acid to the respective DC protein, it is possible to use the probe to distinguish tissue and cell types in situ or in vitro.

This invention also provides reagents which may exhibit significant therapeutic value. The DC proteins (naturally occurring or recombinant), fragments thereof, and antibodies thereto, along with compounds identified as having binding affinity to the DC protein, may be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a DC, e.g., as an antigen presenting cell, is a target for an agonist or antagonist of the protein. The proteins likely play a role in regulation or development of hematopoietic cells, e.g., lymphoid cells, which affect immunological responses, e.g., antigen presentation and the resulting effector functions.

Other abnormal developmental conditions are known in cell types shown to possess DC protein mRNA by northern blot analysis. See Berkow (ed.) *The Merck Manual of Diagnosis and Therapy*. Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions which may be susceptible to prevention or treatment using compositions provided herein.

Recombinant DC proteins or antibodies might be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. In particular, these may be useful in a vaccine context, where the antigen is combined with one of these therapeutic versions of agonists or antagonists. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to these DC proteins, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity might activate the cell through the protein and is thus an agonist in that it simulates the cell. This invention further contemplates the therapeutic use of antibodies to the proteins as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

The DC proteins, fragments thereof, and antibodies to it or its fragments, antagonists, and agonists, could be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, NY; Lieberman, et al. (eds.) (1990) *Pharmaceutical Dosgae Forms: Tablets* Dekker, NY; and Lieberman, et al. (eds.) (1990) *Pharmaceutical Dosage Forms: Disperse Systems* Dekker, NY. The therapy of this invention may be combined with or used in association with other chemotherapeutic or chemopreventive agents.

Both the naturally occurring and the recombinant form of the DC proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, e.g., soluble versions of, DC protein as provided by this invention.

For example, antagonists can often be found once the protein has been structurally defined. Testing of potential protein analogs is now possible upon the development of highly automated assay methods using a purified surface protein. In particular, new agonists and antagonists will be discovered by using screening techniques described herein. Of particular importance are compounds found to have a combined binding affinity for multiple related cell surface antigens, e.g., compounds which can serve as antagonists for species variants of a DC protein.

This invention is particularly useful for screening compounds by using recombinant DC protein in a variety of drug screening techniques. The advantages of using a recombinant protein in screening for specific ligands include: (a) improved renewable source of the protein from a specific source; (b) potentially greater number of antigens per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a DC protein. Cells may be isolated which express that protein in isolation from any others. Such cells, either in viable or fixed form, can be used for standard surface protein binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of DC protein) are contacted and incubated with an antibody having known binding affinity to the antigen, such as $^{125}$I-antibody, and a test sample whose binding affinity to the binding composition is being measured. The bound and free labeled binding compositions are then separated to assess the degree of protein binding. The amount of test compound bound is inversely proportional to the amount of labeled antibody binding to the known source. Many techniques can be used to separate bound from free reagent to assess the degree of binding. This separation step could typically involve a procedure such as adhesion to filters followed by washing, adhesion to plastic followed by washing, or centrifugation of the cell membranes. Viable cells could also be used to screen for the effects of drugs on these DC protein mediated functions, e.g., antigen presentation or helper function.

Another method utilizes membranes from transformed eukaryotic or prokaryotic host cells as the source of a DC protein. These cells are stably transformed with DNA vectors directing the expression of the sppropriate protein, e.g., an engineered membrane bound form. Essentially, the membranes would be prepared from the cells and used in binding assays such as the competitive assay set forth above.

Still another approach is to use solubilized, unpurified or solubilized, purified DC protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to the respective DC protein and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified DC protein, and washed. The next step involves detecting bound reagent, e.g., antibody.

One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

X. Kits

This invention also contemplates use of these DC proteins, fragments thereof, peptides, and their fusion products in a variety of diagnostic kits and methods for detecting the presence of a DC protein or message. Typically the kit will have a compartment containing either a defined DC peptide or gene segment or a reagent which recognizes one or the other, e.g., antibodies.

A kit for determining the binding affinity of a test compound to the respective DC protein would typically comprise a test compound; a labeled compound, for example an antibody having known binding affinity for the protein; a source of the DC protein (naturally occurring or recombinant); and a means for separating bound from free labeled compound, such as a solid phase for immobilizing the DC protein. Once compounds are screened, those having suitable binding affinity to the protein can be evaluated in suitable biological assays, as are well known in the art, to determine whether they act as agonists or antagonists to regulate DC function. The availability of recombinant DC polypeptides also provide well defined standards for calibrating such assays.

A preferred kit for determining the concentration of, for example, a DC protein in a sample would typically comprise a labeled compound, e.g., antibody, having known binding affinity for the DC protein, a source of DC protein (naturally occurring or recombinant) and a means for separating the bound from free labeled compound, for example, a solid phase for immobilizing the DC protein. Compartments containing reagents, and instructions, will normally be provided.

Antibodies, including antigen binding fragments, specific for the respective DC or its fragments are useful in diagnostic applications to detect the presence of elevated levels of the protein and/or its fragments. Such diagnostic assays can employ lysates, live cells, fixed cells, immunofluorescence, cell cultures, body fluids, and further can involve the detection of antigens in serum, or the like. Diagnostic assays may be homogeneous (without a separation step between free reagent and antigen-DC protein complex) or heterogeneous (with a separation step). Various commercial assays exist, such as radioimmunoassay (RIA), enzyme-linked immunosorbentassay (ELISA), enzyme, immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to the DC protein or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY. In particular, the reagents may be useful for diagnosing DC populations in biological samples, either to detect an excess or deficiency of DC in a sample. The assay may be directed to histological analysis of a biopsy, or evaluation of DC numbers in a blood or tissue sample.

Anti-idiotypic antibodies may have similar use to diagnose presence of antibodies against a DC protein, as such may be diagnostic of various abnormal states. For example, overproduction of the DC protein may result in various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled DC protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the protein, test compound, DC protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free protein, or alternatively the bound from the free test compound. The DC protein can be immobilized on various matrices followed by washing. Suitable matrices include plastic such as an ELISA plate, filters, and beads. Methods of immobilizing the DC protein to a matrix include, without limitation, direct adhesion to plastic, use of a capture antibody, chemical coupling, and biotin-avidin. The last step in this approach involves the precipitation of protein/antibody complex by one of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a respective DC protein. These sequences can be used as probes for detecting levels of the message in samples from patients suspected of having an abnormal condition, e.g., cancer or immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XI. Binding Partner Isolation

Having isolated one member of a binding partner of a specific interaction, methods exist for isolating the counterpartner. See, Gearing, et al. (1989) *EMBO J.* 8:3667–3676. For example, means to label a DC surface protein without interfering with the binding to its receptor can be determined. For example, an affinity label can be fused to either the amino- or carboxyl-terminus of the ligand. An expression library can be screened for specific binding to the DC protein, e.g., by cell sorting, or other screening to detect subpopulations which express such a binding component. See, e.g., Ho, et al. (1993) *Proc. Nat'l Acad. Sci. USA* 90:11267–11271. Alternatively, a panning method may be used. See, e.g., Seed and Aruffo (1987) *Proc. Nat'l Acad. Sci. USA* 84:3365–3369. A two-hybrid selection system may also be applied making appropriate constructs with the available DC protein sequences. See, e.g., Fields and Song (1989) *Nature* 340:245–246.

Protein cross-linking techniques with label can be applied to isolate binding partners of a DC protein. This would allow identification of proteins which specifically interact with the appropriate DC protein.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY.

Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1996 and periodic Supplements) *Current Protocols in Protein Science* Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *QIAexpress: The High Level Expression & Protein Purification System* QUIAGEN, Inc., Chatsworth, Calif.

Methods for determining immunological function are described, e.g., in Coligan, et al. (1992 and periodic Supplements) *Current Protocols in Immunology* Wiley/Greene, NY. See also, e.g., Paul (ed.) (1993) *Fundamental Immunology* (3d ed.) Raven Press, N.Y.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Generation of Dendritic Cells

Human CD34+ cells were obtained as follows. See, e.g., Caux, et al. (1995) pages 1–5 in Banchereau and Schmitt *Dendritic Cells in Fundamental and Clinical Immunology* Plenum Press, NY. Peripheral or cord blood cells, sometimes CD34+ selected, were cultured in the presence of Stem Cell Factor (SCF), GM-CSF, and TNF-a in endotoxin free RPMI 1640 medium (GIBCO, Grand Island, N.Y.) supplemented with 10% (v/v) heat-inactivated fetal bovine serum (FBS; Flow Laboratories, Irvine, Calif.), 10 mM HEPES, 2 mM L-glutamine, $5 \times 10^{-5}$ M 2-mercaptoethanol, penicillin (100 mg/ml). This is referred to as complete medium.

CD34+ cells were seeded for expansion in 25 to 75 cm² flasks (Corning, N.Y.) at 2×10⁴ cells/ml. Optimal conditions were maintained by splitting these cultures at day 5 and 10 with medium containing fresh GM-CSF and TNF-a (cell concentration: 1–3×10⁵ cells/ml). In certain cases, cells were FACS sorted for CD1a expression at about day 6.

In certain situations, cells were routinely collected after 12 days of culture, eventually adherent cells were recovered using a 5 mM EDTA solution. In other situations, the CD1a+ cells were activated by resuspension in complete medium at 5×10⁶ cells/ml and activated for the appropriate time (e.g., 1 or 6 h) with 1 mg/ml phorbol 12-myristate 13-acetate (PMA, Sigma) and 100 ng/ml ionomycin (Calbiochem, La Jolla, Calif.). These cells were expanded for another 6 days, and RNA isolated for cDNA library preparation.

III. RNA Isolation and Library Construction

Total RNA is isolated using, e.g., the guanidine thiocyanate/CsCl gradient procedure as described by Chirgwin, et al. (1978) *Biochem.* 18:5294–5299.

Alternatively, poly(A)+ RNA is isolated using the OLIGOTEX mRNA isolation kit (QIAGEN). Double stranded cDNA are generated using, e.g., the SUPERSCRIPT plasmid system (Gibco BRL, Gaithersburg, MD) for cDNA synthesis and plasmid cloning. The resulting double stranded cDNA is unidirectionally cloned, e.g., into pSport1 and transfected by electroporation into ELECTROMAX DH10BTM Cells (Gibco BRL, Gaithersburg, Md.).

IV. Sequencing

DNA isolated from randomly picked clones, or after subtractive hybridization using unactivated cells, were subjected to nucleotide sequence analysis using standard techniques. A Taq DiDeoxy Terminator cycle sequencing kit (Applied Biosystems, Foster City, Calif.) can be used. The labeled DNA fragments are separated using a DNA sequencing gel of an appropriate automated sequencer. Alternatively, the isolated clone is sequenced as described, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Chemical sequencing methods are also available, e.g., using Maxam and Gilbert sequencing techniques.

V. Recombinant DC Gene Construct

Poly(A)⁺ RNA is isolated from appropriate cell populations, e.g., using the FastTrack mRNA kit (Invitrogen, San Diego, Calif.). Samples are electrophoresed, e.g., in a 1% agarose gel containing formaldehyde and transferred to a GeneScreen membrane (NEN Research Products, Boston, Mass.). Hybridization is performed, e.g., at 65° C. in 0.5 M NaHPO₄ pH 7.2, 7% SDS, 1 mM EDTA, and 1% BSA (fraction V) with ³²P-dCTP labeled DC gene cDNA at 10⁷ cpm/ml. After hybridization filters are washed three times at 50° C. in 0.2×SSC, 0.1% SDS, and exposed to film for 24 h.

The recombinant gene construct may be used to generate a probe for detecting the message. The insert may be excised and used in the detection methods described above.

VI. Expression of DC Gene Protein in *E. coli*

PCR is used to make a construct comprising the open reading frame, preferably in operable association with proper promoter, selection, and regulatory sequences. The resulting expression plasmid is transformed into an appropriate, e.g., the Topp5, *E. coli* strain (Stratagene, La Jolla, Calif.). Ampicillin resistant (50 µg/ml) transformants are grown in Luria Broth (Gibco) at 37° C. until the optical density at 550 nm is 0.7. Recombinant protein is induced with 0.4 mM isopropyl-bD-thiogalacto-pyranoside (Sigma, St. Louis, Mo.) and incubation of the cells continued at 20° C. for a further 18 hours. Cells from a 1 liter culture are harvested by centrifugation and resuspended, e.g., in 200 ml of ice cold 30% sucrose, 50 mM Tris HCl pH 8.0, 1 mM ethylenediaminetetraacetic acid. After 10 min on ice, ice cold water is added to a total volume of 2 liters. After 20 min on ice, cells are removed by centrifugation and the supernatant is clarified by filtration via a 5 µM Millipak 60 (Millipore Corp., Bedford, Mass.).

The recombinant protein is purified via standard purification methods, e.g., various ion echange chromatography methods. Immunoaffinity methods using antibodies described below can also be used. Affinity methods may be used where an epitope tag is engineered into an expression construct.

VII. Mapping of Human DC Genes

DNA isolation, restriction enzyme digestion, agarose gel electrophoresis, Southern blot transfer and hybridization are performed according to standard techniques. See Jenkins, et al. (1982) *J. Virol.* 43:26–36. Blots may be prepared with Hybond-N nylon membrane (Amersham). The probe is labeled with ³²P-dCTP; washing is done to a final stringency, e.g., of 0.1×SSC, 0.1% SDS, 65° C.

Alternatively, a BIOS Laboratories (New Haven, Conn.) mouse somatic cell hybrid panel may be combined with PCR methods. See Fan, et al. (1996) *Immunogenetics* 44:97–103.

Chromosomal localization with a Stanford G3 panel gave as closest marker SHGC-12041, with a lod of 7.7. This marker, which is the gene coding for M130 antigen, is localized to chromosome 12p13. This localization is host to a number of genes encoding receptors of the C-type lectin family, notably CD69, and the NK receptor family.

VIII. Analysis of Individual Variation

From the distribution data, an abundant easily accessible cell type is selected for sampling from individuals. Using PCR techniques, a large population of individuals are analysed for this gene. cDNA or other PCR methods are used to sequence the corresponding gene in the different individuals, and their sequences are compared. This indicates both the extent of divergence among racial or other populations, as well as determining which residues are likely to be modifiable without dramatic effects on function.

IX. Preparation of Antibodies

Recombinant DC proteins are generated by expression in *E. coli* as shown above, and tested for biological activity. Alternatively, natural protein sources may be used with purification methods made available. Antibody reagents may be used in immunopurification, or to track separation methods. Active or denatured proteins may be used for immunization of appropriate mammals for either polyclonal serum production, or for monoclonal antibody production.

X. Isolation of Counterpart Primate or Rodent DC Genes

Human cDNA clones encoding these genes are used as probes, or to design PCR primers to find counterparts in various primate species, e.g., chimpanzees.

Bioinformatics searches of the EST databases (GenBank dbEST) using the predicted polypeptide sequence of DCMP1 (tblastn algorithm) revealed mouse clones encoding a protein homologous to primate DCMP1. Four clones corresponding to this sequence were seen: AA387662 Ko mouse embryo 11 5dpc; AA170532 mouse spleen; AA475012 mouse mammary gland; and AA423158 mouse mammary gland. One of these, AA170532, estimated to be a full length clone by sequence analysis was selected and DNA sequenced. This clone contained features similar to DCMP1. The full length clone is 1418 bp, excluding the poly-A sequence and contains a 5' UTR of 278 bp. As for hDCMP1, the putative start codon is not contained within a consensus Kozak region, but this codon is preceeded by an upstream stop codon. The 5' UTR contains sequences similar to rapid degradation signals, including three consensus ATTTA sites. A potential polyadenylation sequence is seen. The predicted polypeptide is about 238 residues in length and codes for a type II membrane protein with an ITIM and a C-type lectin domain. Three potential N-glycosylation sites are seen. Alignments of this and the human protein show about 54% identity, 65% homology over the whole sequence. Notably, the ITIM domains are highly conserved (13 out of 15 residues are identical). Of interest is the conserved membrane-proximal glutamine motif (FQKYSQLLE), and the cysteine residue potentially implicated in disulphide bridge formation. Equally the C-type lectin domains show blocks of conservation, including the EPS motif. Differences seen between hDCMP1 and the human hepatic lectins are retained in the mouse sequence, notably the replacement of tryptophan at position 119 and 163; a glutamine at position 177; and serine instead of tryptophan at position 228. It thus appears that this clone is the mouse homologue of hDCMP1.

XI. Use of Reagents to Analyze Cell Populations

Detection of the level of dendritic cells present in a a sample is important for diagnosis of aberrant disease conditions. For example, an increase in the number of dendritic cells in a tissue or the lymph system can be indicative of the presence of a DC hyperplasia, or tissue or graft rejection. A low DC population can indicate an abnormal reaction to, e.g., a bacterial or viral infection, which may require the appropriate treat to normalize the DC response.

FACS analysis using a labeled binding agent specific for a cell surface DC protein, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y., is used in determining the number of DCs present in a cell mixture, e.g., PBMCs, adherent cells, etc. The binding agent is also used for histological analysis of tissue samples, either fresh or fixed, to analyze infiltration of DC. Diverse cell populations may also be evaluated, either in a cell destructive assay, or in certain assays where cells retain viability.

Analysis of the presence of soluble intracellular molecules is performed, e.g., with a fluorescent binding agent specific for a DC as described in Openshaw, et al. (1995) *J. Exp. Med.* 182:1357–1367. Alternatively, tissue or cell fixation methods may be used.

Levels of DC transcripts are quantitated, e.g., using semiquantitative PCR as described in Murphy, et al. (1993) *J. Immunol. Methods* 162:211–223. Primers are designed such that genomic DNA is not detected.

XII. Expression Distribution

Analysis of the entire DCMP1 cDNA sequence in a sequence database revealed an expression pattern restricted to a limited number of libraries. The greatest number of sequences (ten) were detected in Dendritic Cell libraries, four sequences in a library of osteoclastoma cells, and single sequences from libraries of macrophages generated in vitro from monocytes, LPS activated neutrophils, chondrosarcoma, colon cancer, T-cell lymphoma, skin tumor and chronic synovitis. In the GenBank dbEST, four clones were detected: AA418441, subtracted library; AA446401, total fetus; AA677149, fetal liver spleen; C01555, Human Gene Signature; AA380065, Skin tumor.

Analysis of DCMP1 expression by RT-PCR over a number of different cell lines and freshly isolated cells showed that expression of DCMP1 is not detected in TF1 (Myeloid precursor), Jurkat (a T cell line), CHA (kidney carcinoma), MRC5 (fetal lung fibroblasts), JY (B cell line), U937 (myelo-monocytic lymphoma cell line), but is restricted to haematopoeitic cells. In freshly isolated cells, expression is seen in DC, both non-activated and activated; granulocytes activated; PBL, both non-activated and activated; and a low level of expression is seen in monocytes activated; and B cells activated. All activated samples were pools of cells treated with PMA/ionomycin for 1 and 6 hours.

Additional analysis showed that expression of DCMP1 varied with the activation state of the cell. RT-PCR was also used to detect the expression of DCMP1 under different activation states. B cells isolated from tonsillar tissue were treated with PMA/ionomycin for 1 or 6 hours or by coculture with CD40L-expressing L cells for 3, 12, and 24 hours. mRNA was detected in non-activated cells. This expression could be lost within 1 hour for PMA/ionomycin treatment and after 3 hours of CD40L treatment. In contrast, no expression could be detected in T cells, even after anti-CD3/anti-CD28 incubation.

In CD34+ derived cells expression of DCMP1 was strong in macrophages derived from CD34+ progenitor cells in the presence of M-CSF. This expression did not appear to alter in response to PMA/ionomycin. In DC derived from CD34+ progenitor cells in the presence of GM-CSF and TNFa, the level of mRNA was seen to vary over the time course of culture, with greater amounts of mRNA detected at day 12 of culture. After 48 hours of coculture with CD40L bearing L cells, the expression of DCMP1 is lost. In in vitro DC FACS sorted at day 6 for the presence of markers CD1a/CD14 and continued in culture for a further 6 days, more mRNA was detected in the CD14 than in the CD1a subpopulation. This expression was down-regulated by PMA/ionomycin treatment.

In monocytes isolated from blood, no mRNA was detected in non-activated cells. However, expression of DCMP1 was detected after 6 hours of treatment with PMA/ionomycin. In DC derived from monocytes by treatment with GM-CSF and IL-4, DCMP1 expression was upregulated. This expression could not be altered by treatment with PMA/ionomycin, but could be downregulated by coculture with CD40L expressing L cells. In this case DCMP1 mRNA expression was totally lost by 24 hours of culture. Expression of the human protein was cinfirmed using antibody detection methods.

DCMP1 was expressed in subsets of DC isolated ex vivo. DC subsets isolated from blood or from tonsillar tissue were characterized by the presence or absence of the integrin CD11c. Larson and Springer (1990) *Immunol. Rev.* 114: 181–217. The CD11c+ subset of DC isolated from blood (also known as GCDC) express DCMP1. However, no mRNA is detected after activation via an anti-CD40L or PMA/ionomycin treatment. In contrast, the same subset of cells isolated from tonsillar tissue no longer express DCMP1. In the case of the CD11c-DC subset, a low level of expression is observed in cells isolated from blood. This expression is greater in cells isolated from tonsillar tissue, but again is downregulated on activation via an anti-CD40 antibody or with PMA/ionomycin treatment. Langerhans cells isolated from skin express DCMP1, while the surrounding basal cells show no expression.

XIII. Primate DCMP1

Sequence analysis suggests these DCMPs are members of the lectin/asialoglycoprotein superfamily of receptors. In particular, the heapatic and macrophage lectins have been associated with the internalization of proteins and peptides, which, e.g., might be important in the uptake and presentation of antigen by dendritic cells. The DCMP1 contains an internalization motif (YxxV) or an ITIM-like motif (Ix-YxxV; residues 5–10 of SEQ ID NO: 2; a more extended motif runs from residues 1 to 24). This suggests that the protein may be a dendritic cell version of the family of Inhibitory Receptors (KIR; LIR, etc.), which send a negative signal to inhibit cell function.

The putative open reading frame commences at about nucleotide 242. This potential start codon is not in a consensus Kozak sequence, but since it is not preceeded by an alternative ATG and a stop codon exists at upstream position 200, it is predicted that this is the start of the encoded protein. A polypeptide of about 237 amino acids was predicted from this sequence. No signal peptide was detected, but a putative transmembrane sequence extends from positions about 386 to 443. This clone encodes a type II membrane protein with a C-type lectin domain. The 3' UTR contains a number of potential rapid degradation signals, including three repeats of the consensus sequence ATTTA. No signal peptide was detected, but putative transmembrane sequences extend from positions 45 to 62, or alternatively, 386 to 443. This clone encodes a type II membrane protein with a C-type lectin domain.

The polypeptide predicted from the sequence analysis has a 49 amino acid intracellular domain which includes a tyrosine-based motif centred at residue 7. YXX(L/V) motifs of this nature have been shown to act as internalization motifs in the case of the hepatic lectins and CD23 (Fce RIIa). This type of domain has been shown to act as activation (ITAM) or inhibitory (MM) motifs in molecules such as Ly49, NKG2A, and the KIR family of immunoglobulin-like molecules. Inhibition is mediated by the recruitment of SHP2/SHIP phosphatases to the consensus domain (I/V)XYXX(L/V). The first 15 amino acids of DCMP1 show conservation to the extended ITIM domain, and it seems likely that inhibition of cell function is one of the attributes of DCMP1. A single potential N-glycosylation site is present at about position 185.

Comparison of the amino acid sequence of the C-type lectin domain of DCMP1 with other proteins containing C-type lectin domains showed that DCMP1 has the greatest homology to the hepatic lectins and the macrophage lectin (see Table 1). The conserved cysteine residues of the C-type lectin fold are clearly conserved across the members of this family, however a number of distinguishing features can be seen. Like the hepatic lectins, DCMP1 has a double cysteine motif at the start of the lectin domain. The function of this supplementary cysteine is unknown as there is apparently no other cysteine in the lectin domain that may form a disulphide bridge with this residue. It is possible that this residue may be involved in intermolecular disulphide bridge formation, although there is another cysteine in DCMP1 at position 91 which probably fulfils this function. The N-terminal portion of the DCMP1 lectin domain shows greatest conservation with the hepatic lectins and the macrophage lectin. The calcium-binding domain is conserved in DCMP1 and shows greatest homology to CD23, including the EPS motif (residues 195–197), glutamate (E) at position 201 and asparagine aspartate (ND) at position 218–219. These motifs are noticeably absent from the NK receptors (NKGE shown here) and CD94.

The DCMP1 is a type II membrane protein with the predicted transmembrane segment from about residues 45 to 62. It is related to the family of proteins which includes asialoglycoprotein receptors, hepatic lectins, CD69, CD72, CD23, and NK receptors. This protein contains an extracellular Ca dependent C-type lectin domain at the carboxy terminus (from about residues 104 to 237), which exhibits the motifs characteristic of sugar residue specificity. See Table 1. These proteins typically bind to sugar residues on glycoproteins and are implicated in the primary immune response. Several members of this family, notably CD69, the NK receptors, and CD72, have been shown to transmit a signal during cellular activation events including proliferation and the induction of specific genes.

DCMP1, like the mouse C-type lectin KIR receptor, Ly 49, contains an internalisation motif with extended homology to the group of inhibitory receptors (ITIM domain, see recent reviews by Vivier and Daeron (1997) *Immunology Today* 18:286–291; and Katz and Austen (1997) *J. Immunol.* 158:5065–5070). These receptors, either Immunoglobulin superfamily (IgSF) members or C-type lectins, transmit a negative signal via SH2-domain containing phosphatases, e.g., SHIP, SHP-1, and SHP-2. Evidence suggests that these receptors associate with other activation receptors in order to block activation signals. Evidence also suggests that the ligand for this type of molecule is an IgSF molecule. Examples of this are the MHC class I molecules (recognised by the CD94/NK receptors and Ly-49) and the FcgR (CD23; which recognises IgG).

The cysteine residue 91 is likely to be involved in disulfide linkage to another polypeptide, perhaps a homo or heterodimer.

PCR analysis indicates that the gene is expressed in activated dendritic cells and non-activated dendritic cells. Detectable signals were not found in any of TF1 (hematopoietic cell line), Jurkat (T cell line), MRC5 (lung fibroblast sarcoma cell line), JY (B cell line), U937 (pre-monocyte cell line), or CHA (carcinoma cell line) cells. Positive signals were detected in freshly isolated activated or non-activated PBLs, and granulocytes, but only weak signals from freshly isolated T cells, B cells, NK cells, or monocytes.

Sequence analysis indicates expression of the gene in samples characterized as dendritic cells, activated neutrophils, macrophages (activated with GM-CSF), osteoclastoma, skin tumor, T-cell lymphoma, colon cancer, chronic synovitis, and chrondrosarcoma.

TABLE 2

The sequence shows homology to two ESTs of mouse, W33446
(see SEQ ID NO: 11) and AA170532 (see SEQ ID NO: 8) which
code for the mouse counterpart of DCMP1 (see SEQ ID NO: 8).

```
hDCMP1    MTSEITYAEVRFKNEFKSSGINTASSAASKERTAPLKSNTGFPKLLCASL
W33446    --------------------------------------------------
170532    MASEITYAEVKFKNESNSLHTYSESPAAPREKPIRDLRKPGSPSLLLTSL
mDCMP1    MASEITYAEVKFKNESNSLHTYSESPAAPREKPIRDLRKPGSPSLLLTSL hDCMP1    LIFFLLLAISFFIAFVIFFQKYSQLLE-KKTTKELVHTTLECVKKNMPVE
W33446    -------------------------E-KMIIKELNYTELECTKWASLLE
170532    MLLLLLLAITFLVAFIIYFQKYSQLLEEKKAAKNIM
mDCMP1    MLLLLLLAITFLVAFIIYFQKYSQLLEEKKAAKNIMHNELNCTKSVSPME hDCMP1    ETAWSCCPKNWKSFSSNCYFISTE--SASWQDSEKDCARMEAHLLVINTQ
W33446    DKVWSCCPKDWKPFGSYCYFTSTD-LVASWNESKENCFHMGAHLVVIHSQ
mDCMP1    DKVWSCCPKDWRLFGSHCYLVPTVSSSASWNKSEENCSRMGAHLVVIQSQ
hDCMP1    EEQDFIFQNLQEESAYFVGLSDPEGQRHWQWVDQTPYNESSTFWHPREPS
W33446    EEQ
mDCMP1    EEQDFITGILDTHAAYFIGLWD-TGHRQWQWVDQTPYEESITFWHNGEPS hDCMP1    DPNERCVVLNFR-KSPKRWGWNDVNCLGPQRSVCEMMKIHL
mDCMP1    SGNEKCATIIYRWKT--GWGWNDISCSLKQKSVCPMKKINL
```

Table 2: The sequence shows homology to two ESTs of mouse, W33446 (see SEQ ID NO: 11) and AA170532 (see SEQ ID NO: 8) which code for the mouse counterpart of DCMP1 (se SEQ ID NO: 8). Also shown is hDCMP1 (SEQ ID NO: 2).

XV. Primate DCMP2

DCMP2, a putative asialoglycoprotein receptor, is a type II transmembrane protein. In its extracellular region, DCMP2 features a single carbohydrate recognition domain (CRD), characteristic of the C-type (Ca++ dependent) family of lectins (see Drickamer and Taylor (1993) *Ann. Rev. Cell Biol.* 9:237–264. DCMP2 displays considerable homology with the two genes (HI and H2) encoding the subunits of the human hepatic asialoglycoprotein-receptor. Stockert (1995) *Physiol. Revs.* 75:591–609. These hepatic receptors represent the prototype of the type II C-type lectin family members. Liver ASGPR has binding specificity for desialylated glycoproteins displaying terminal galactosyl residues, and mediates their endocytosis into hepatocytes via the clathrin-coated pit pathway. Notably, the features associated with both these functions are conserved between the hepatic ASGPR and DCMP2. Thus, DCMP2 contains an intracellular motif including a tyrosine residue at position 5 and which is associated with ligand endocytosis capacity. See Fuhrer, et al. (1991) *J. Cell Biol.* 114:423–431. In addition, the DCMP2 display a QPD (Gln-Pro-Asp) galactose-recognition type sequence (Drickamer (1992) *Nature* 360:183–186) in its sugar recognition domain.

Several variant cDNA clones encoding the DCMP2 have been isolated, most likely as a consequence of alternative splicing. Three variants are described hereunder: a short form, a long form, and a third form designated DCMP2v. See SEQ ID NO: 4 and 10; Table 1. The short and long forms differ by the presence of a unique 27 aa insert in the extracellular region of the short form clone. The short form of the DCMP2 exhibits 4 residue differences in the extracellular region to a recently cloned ASGPR obtained from human macrophages (M-ASGPR). Suzuki, et al. (1996) *J. Immunol.* 156:128–135.

Relative to the DCMP21, the ASGPRm lacks the seqment corresponding to GVSELQEHTTQKAHLGHCPHCPS-VCVP (residues 118–144 of SEQ ID NO: 4), and the ASGPRm contains an insert of GEE (between residues 173 and 174 of SEQ ID NO: 4). The DCMP2s is identical to the DCMP21, except for the absence of the GVSELQEHTTQ-KAHLGHCPHCPSVCVP (residues 118–144 of SEQ ID NO: 4), and a difference in sequence at nucleotide 1064 from G to A, thereby encoding asn rather than asp. The DCMPv is similar to DCMPs, but lacks the sequence LLQRLRSG-PCHLLLSLGLG (residues 30–48 of SEQ ID NO: 4), which corresponds to a significant portion of the transmembrane segment; and contains the insert of GEE (between residues 173 and 174 of SEQ ID NO: 4) as found in the ASGPRm. Regions surrounding these differences, e.g., within an epitope length, e.g., 12–17 amino acids, are of interest.

Recombinant DCMP2 long form protein is available, and mABs have been generated. In addition, a murine cell line has been transfected for stable expression of both the long and short forms.

The gene was originally isolated from 70% pure CD1a$^+$ DC derived from CD34$^+$ hematopoietic progenitor cells cultured in GM-CSF and TNFa (Caux, et al. (1992) *Nature* 360:258–261. The clone has been inserted into a pSport1 vector (NotI/SalI restriction sites).

PCR analysis suggests expression of DCMP2 genes in dendritic cells, and perhaps very weakly in TF1 (hematopoietic cell line) cells. There was not detectable signal from Jurkat (T cell line), CHA (carcinoma cell line), MRC5 (lung fibroblast sarcoma cell line), or JY (B cell line). Signal was detected in freshly isolated non-activated or activated (PMA and ionomycin) dendritic cells, granulocytes, and non-activated or activated PBL. Signal was not detected in monocytes, non-activated or activated T cells, or non-activated or activated B cells.

DC-ASPGR displays considerable homology with the murine counterpart of human monocyte ASGPR (M-ASGPR). Homology is striking (~60%) within the carbohydrate-recognition domain which confers specificity to murine monocyte ASGPR for galactose and N-acetylgalactosamine (GalNAc). Sato, et al. (1992) *J. Biochem.* 111: 331–336. This includes the QPD motif, also found in the H1 and H2 subunits of the hepatic ASGPR. In addition, murine monocyte ASGPR has a YENL internalization signal in its cytosolic domain.

Murine M-ASGPR functions as a receptor for endocytosis of galactosylated glycoproteins (Ozaki, et al. (1992) *J. Biol.*

Chem. 267:9229–9235), and allows recognition of malignant cells by tumoricidal macrophages (Kawakami, et al. (1994) *Jpn. J. Cancer Res.* 85:744–749). In this context, murine M-ASGPR was found to be expressed within lung metastatic nodules of mice bearing OV2944-HM-1 metastatic ovarian tumor cells (Imai,.et al. (1995) *Immunol.* 86:591–598). Of interest, human M-ASGPR demonstrates a remarkable specificity for Tn antigen (Suzuki, et al. (1996) *J. Immunol.* 156:128–135), which bears a cluster of serine or threonine-linked terminal GalNAc, and is associated with human carcinomas (Springer (1989) *Mol. Immunol.* 26:1–5; and Ørntoft, et al. (1990) *Int. J. Cancer* 45:666–672).

On the basis of sequence homology, it can be predicted that DCMPs also function as an endocytic receptor for galactosylated glycoproteins. In addition, ligand internalization via the mannose-receptor, another C-type transmembrane endocytic lectin, results in highly efficient antigen-presentation by DC through the MHC class II pathway. Cella, et al. (1997) *Current Opinion Immunol.* 9:10–16. By analogy, it is possible that the DCMPs play a similar role in routing internalized ligands into an antigen-presentation pathway.

Thus, DCMP2 could be a potential high-efficiency target for loading antigens into DC for enhancing presentation to T cells in immune-based adjuvant therapy. This could be approached by pulsing DC in vitro either with a galactosylated form of antigen, or with anti-DCMP2 mAbs coupled to antigen. In vitro efficiency of presentation could be assayed by activation of antigen-specific T cells. This would focus on presentation of tumor-associated antigens (TAA), due to the inherent therapeutic perspectives of such an approach. Of particular interest are TAA associated with malignant melanoma.

In addition, the specificity of human M-ASGPR for Tn antigen makes this carcinoma TAA a candidate of choice for targeting the DCMP2.

As has been recently shown that exogenous antigen can be processed and presented in the MHC class I pathway. See Porgador and Gilboa (1995) *J. Exp. Med.* 182:255–260; Paglia, et al. (1996) *J. Exp. Med.* 183:317–322. Specialized receptors are likely to perform such a function in DC.

These receptors in DC may be targetted to help produce TAA-specific cytotoxic T cells (CTL), with significant therapeutic potential, as CTL appear to be implicated in the induction of tumor rejection.

XVI. DCMP Internalization

DC obtained from CD34+ progenitors cultured in GM-CSF and TNFa were stained at 4° C. with anti-DCMP2 mAb, or anti-CD13 as control. Following subsequent incubation at 37° C. for a period of up to about 20 min, cell surface bound mAbs were analyzed. Internalization was observed by decrease in cell surface fluorescence.

The DCMP21 is rapidly internalized at 37° C., but not at 4° C. About 60% of the surface label disappeared within about 15 min. This demonstrates that the DCMP2 can function as an endocytic receptor, consistent with the presence of an internalization motif (YENF) in its intracytoplasmic domain.

XVII. Isolation of a Binding Counterpart

A DC protein can be used as a specific binding reagent, by taking advantage of its specificity of binding, much like an antibody would be used. A binding reagent is either labeled as described above, e.g., fluorescence or otherwise, or immobilized to a substrate for panning methods.

The DC protein is used to screen for a cell line which exhibits binding. Standard staining techniques are used to detect or sort intracellular or surface expressed ligand, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×10$^5$ cells per chamber in 1.5 ml of growth media. Incubate overnight at 37° C.

On day 1 for each sample, prepare 0.5 ml of a solution of 66 mg/ml DEAE-dextran, 66 mM chloroquine, and 4 mg DNA in serum free DME. For each set, a positive control is prepared, e.g., of human receptor-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin(0.1%) with 32 ml/ml of 1M NaN$_3$ for 20 min. Cells are then washed with HBSS/saponin 1×. Add protein or protein/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, other monocyte protein specific binding reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a monocyte protein fusion construct, or by use of antibodies raised against the first antibodies. Recursive cycles of selection and amplification lead to enrichment of appropriate clones and eventual isolation of ligand expressing clones.

Phage expression libraries can be screened by monocyte protein. Appropriate label techniques, e.g., anti-FLAG antibodies, will allow specific labeling of appropriate clones.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant nucleic acid encoding the polypeptide of SEQ ID NO: 4.

2. The nucleic acid of claim 1, wherein the nucleic acid comprises nucleotides 257–1204 of SEQ ID NO: 3.

3. An expression vector comprising the nucleic acid of claim 1 or 2.

4. A host cell comprising the vector of claim 3.

5. A process for recombinantly producing the polypeptide of SEQ ID NO:4 comprising culturing the host cell of claim 4 under conditions in which the polypeptide is expressed.

6. An isolated or recombinant nucleic acid encoding amino acids 118–144 of SEQ ID NO: 4.

7. The nucleic acid of claim 6, wherein the nucleic acid comprises nucleotides 608–688 of SEQ ID NO: 3.

8. An expression vector comprising the nucleic acid of claim 6 or 7.

9. A host cell comprising the vector of claim 8.

10. A process for recombinantly producing a polypeptide comprising amino acids 118–144 of SEQ ID NO:4 comprising culturing the host cell of claim 9 under conditions in which the polypeptide is expressed.

* * * * *

SEQUENCE LISTING

<160> NUMBER OF SEQ ID NOS: 13

<210> SEQ ID NO 1
<211> LENGTH: 1104
<212> TYPE: DNA
<213> ORGANISM: Unknown
<220> FEATURE:
<223> OTHER INFORMATION: mammalian nucleic acid and protein
<220> FEATURE:
<221> NAME/KEY: CDS
<222> LOCATION: (242)..(952)
<223> OTHER INFORMATION:

<400> SEQUENCE: 1

```
ttctcactat actggtcctg aggaaagggc ttctgtgaac tgcggttttt agtttttatt      60
gtggttctta gttctcatga gacccctctt gaggatatgt gcctatctgg tgcctctgct     120
ctccactagt tgagtgaaag gaaggaggta atttaccacc atgtttggtt cctgtttata     180
agatgtttta agaaagattt gaacagatt ttctgaagaa gcagaagct ctcttcccat       240 t atg act tcg gaa atc act tat gct gaa gtg agg ttc aaa aat gaa ttc    289
  Met Thr Ser Glu Ile Thr Tyr Ala Glu Val Arg Phe Lys Asn Glu Phe
  1               5                  10                  15 aag tcc tca ggc atc aac aca gcc tct tct gca gct tcc aag gag agg      337
Lys Ser Ser Gly Ile Asn Thr Ala Ser Ser Ala Ala Ser Lys Glu Arg
            20                  25                  30 act gcc cct ctc aaa agt aat acc gga ttc ccc aag ctg ctt tgt gcc      385
Thr Ala Pro Leu Lys Ser Asn Thr Gly Phe Pro Lys Leu Leu Cys Ala
        35                  40                  45 tca ctg ttg ata ttt ttc ctg cta ttg gca atc tca ttc ttt att gct      433
Ser Leu Leu Ile Phe Phe Leu Leu Leu Ala Ile Ser Phe Phe Ile Ala
    50                  55                  60 ttt gtc att ttc ttt caa aaa tat tct cag ctt ctt gaa aaa aag act      481
Phe Val Ile Phe Phe Gln Lys Tyr Ser Gln Leu Leu Glu Lys Lys Thr
65                  70                  75                  80 aca aaa gag ctg gtt cat aca aca ttg gag tgt gtg aaa aaa aat atg      529
Thr Lys Glu Leu Val His Thr Thr Leu Glu Cys Val Lys Lys Asn Met
                85                  90                  95 ccc gtg gaa gag aca gcc tgg agc tgt tgc cca aag aat tgg aag tca      577
Pro Val Glu Glu Thr Ala Trp Ser Cys Cys Pro Lys Asn Trp Lys Ser
            100                 105                 110 ttt agt tcc aac tgc tac ttt att tct act gaa tca gca tct tgg caa      625
Phe Ser Ser Asn Cys Tyr Phe Ile Ser Thr Glu Ser Ala Ser Trp Gln
        115                 120                 125 gac agt gag aag gac tgt gct aga atg gag gct cac ctg ctg gtg ata      673
Asp Ser Glu Lys Asp Cys Ala Arg Met Glu Ala His Leu Leu Val Ile
    130                 135                 140 aac act caa gaa gag cag gat ttc atc ttc cag aat ctg caa gaa gaa      721
Asn Thr Gln Glu Glu Gln Asp Phe Ile Phe Gln Asn Leu Gln Glu Glu
145                 150                 155                 160 tct gct tat ttt gtg ggg ctc tca gat cca gaa ggt cag cga cat tgg      769
Ser Ala Tyr Phe Val Gly Leu Ser Asp Pro Glu Gly Gln Arg His Trp
                165                 170                 175 caa tgg gtt gat cag aca cca tac aat gaa agt tcc aca ttc tgg cat      817
Gln Trp Val Asp Gln Thr Pro Tyr Asn Glu Ser Ser Thr Phe Trp His
            180                 185                 190 cca cgt gag ccc agt gat ccc aat gag cgc tgc gtt gtg cta aat ttt      865
Pro Arg Glu Pro Ser Asp Pro Asn Glu Arg Cys Val Val Leu Asn Phe
        195                 200                 205 cgt aaa tca ccc aaa aga tgg ggc tgg aat gat gtt aat tgt ctt ggt      913
Arg Lys Ser Pro Lys Arg Trp Gly Trp Asn Asp Val Asn Cys Leu Gly
```

-continued

```
Arg Lys Ser Pro Lys Arg Trp Gly Trp Asn Asp Val Asn Cys Leu Gly
    210                 215                 220 cct caa agg tca gtt tgt gag atg atg aag atc cac tta tgaactgaac    962
Pro Gln Arg Ser Val Cys Glu Met Met Lys Ile His Leu
225             230                 235 attctccatg aacaggtggt tggattggta tctgtcattg tagggataga taataagctc  1022
ttcttattca tgtgtaaggg aggtccatag aatttaggtg gtctgtcaac tattctactt  1082
atgagagaat tggtctgtac at                                          1104
```

<210> SEQ ID NO 2
<211> LENGTH: 237
<212> TYPE: PRT
<213> ORGANISM: Unknown
<220> FEATURE:
<223> OTHER INFORMATION: mammalian nucleic acid and protein

<400> SEQUENCE: 2

```
Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro Leu Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
65                  70                  75                  80

Thr Lys Glu Leu Val His Thr Thr Leu Glu Cys Val Lys Lys Asn Met
                85                  90                  95

Pro Val Glu Glu Thr Ala Trp Ser Cys Cys Pro Lys Asn Trp Lys Ser
            100                 105                 110

Phe Ser Ser Asn Cys Tyr Phe Ile Ser Thr Glu Ser Ala Ser Trp Gln
        115                 120                 125

Asp Ser Glu Lys Asp Cys Ala Arg Met Glu Ala His Leu Leu Val Ile
    130                 135                 140

Asn Thr Gln Glu Glu Gln Asp Phe Ile Phe Gln Asn Leu Gln Glu Glu
145                 150                 155                 160

Ser Ala Tyr Phe Val Gly Leu Ser Asp Pro Glu Gly Gln Arg His Trp
                165                 170                 175

Gln Trp Val Asp Gln Thr Pro Tyr Asn Glu Ser Ser Thr Phe Trp His
            180                 185                 190

Pro Arg Glu Pro Ser Asp Pro Asn Glu Arg Cys Val Val Leu Asn Phe
        195                 200                 205

Arg Lys Ser Pro Lys Arg Trp Gly Trp Asn Asp Val Asn Cys Leu Gly
    210                 215                 220

Pro Gln Arg Ser Val Cys Glu Met Met Lys Ile His Leu
225             230                 235
```

<210> SEQ ID NO 3
<211> LENGTH: 1458
<212> TYPE: DNA
<213> ORGANISM: Unknown
<220> FEATURE:
<223> OTHER INFORMATION: mammalian nucleic acid and protein
<220> FEATURE:
<221> NAME/KEY: CDS
<222> LOCATION: (257)..(1204)
<223> OTHER INFORMATION: protein coding sequence -continued

```
<220> FEATURE:
<221> NAME/KEY: misc_feature
<222> LOCATION: (608)..(673)
<223> OTHER INFORMATION: short form lacks nucleotides 608-673
<220> FEATURE:
<221> NAME/KEY: misc_feature
<222> LOCATION: (775)..(776)
<223> OTHER INFORMATION: ASGPRm (Table 2) has sequence insert encoding
      GEE between nucleotides 775-776
<220> FEATURE:
<221> NAME/KEY: misc_feature
<222> LOCATION: (1064)..(1064)
<223> OTHER INFORMATION: nucleotide 1064 of DCMP2s may be A, which would
      encode Asn rather than Asp at the residue numbered 270

<400> SEQUENCE: 3
gttgaggaga tgggatgtcc cagatgatag ggctcctggg atttcagacc caagaccagc      60
aggactccag tcacctctac cccagctctc caggacacag cgctcccaac tctgagtgac     120
gtcccacctc tggtccttgc agcacaacca acgtgggaat cacaccctcc agacctccca    180
cagctccacc ccagactggg cgccggccct gcctccattt cagctgtgac aacctcagag    240
ccgtgttggc ccaagc atg aca agg acg tat gaa aac ttc cag tac ttg gag    292
               Met Thr Arg Thr Tyr Glu Asn Phe Gln Tyr Leu Glu
                 1               5                  10 aat aag gtg aaa gtc cag ggg ttt aaa aat ggg cca ctt cct ctc cag      340
Asn Lys Val Lys Val Gln Gly Phe Lys Asn Gly Pro Leu Pro Leu Gln
         15                  20                  25 tcc ctc ctg cag cgt ctc cgc tct ggg ccc tgc cat ctc ctg ctg tcc      388
Ser Leu Leu Gln Arg Leu Arg Ser Gly Pro Cys His Leu Leu Leu Ser
 30                  35                  40 ctg ggc ctc ggc ctg ctg ctg gtc atc atc tgt gtg gtt gga ttc          436
Leu Gly Leu Gly Leu Leu Leu Val Ile Ile Cys Val Val Gly Phe
45                  50                  55                  60 caa aat tcc aaa ttt cag agg gac ctg gtg acc ctg aga aca gat ttt      484
Gln Asn Ser Lys Phe Gln Arg Asp Leu Val Thr Leu Arg Thr Asp Phe
                 65                  70                  75 agc aac ttc acc tca aac act gtg gcg gag atc cag gca ctg act tcc      532
Ser Asn Phe Thr Ser Asn Thr Val Ala Glu Ile Gln Ala Leu Thr Ser
             80                  85                  90 cag ggc agc agc ttg gaa gaa acg ata gca tct ctg aaa gct gag gtg      580
Gln Gly Ser Ser Leu Glu Glu Thr Ile Ala Ser Leu Lys Ala Glu Val
         95                  100                 105 gag ggt ttc aag cag gaa cgg cag gca ggg gta tct gag ctc cag gaa      628
Glu Gly Phe Lys Gln Glu Arg Gln Ala Gly Val Ser Glu Leu Gln Glu
     110                 115                 120 cac act acg cag aag gca cac cta ggc cac tgt ccc cac tgc cca tct      676
His Thr Thr Gln Lys Ala His Leu Gly His Cys Pro His Cys Pro Ser
125                 130                 135                 140 gtg tgt gtc cca gtt cat tct gaa atg ctc ctg cga gtc cag cag ctg      724
Val Cys Val Pro Val His Ser Glu Met Leu Leu Arg Val Gln Gln Leu
                 145                 150                 155 gtg caa gac ctg aag aaa ctg acc tgc cag gtg gct act ctc aac aac      772
Val Gln Asp Leu Lys Lys Leu Thr Cys Gln Val Ala Thr Leu Asn Asn
             160                 165                 170 aat gcc tcc act gaa ggg acc tgc tgc ccc gtc aac tgg gtg gag cac      820
Asn Ala Ser Thr Glu Gly Thr Cys Cys Pro Val Asn Trp Val Glu His
         175                 180                 185 caa gac agc tgc tac tgg ttc tct cac tct ggg atg tcc tgg gcc gag      868
Gln Asp Ser Cys Tyr Trp Phe Ser His Ser Gly Met Ser Trp Ala Glu
     190                 195                 200 gct gag aag tac tgc cag ctg aag aac gcc cac ctg gtg gtc atc aac      916
Ala Glu Lys Tyr Cys Gln Leu Lys Asn Ala His Leu Val Val Ile Asn
```

-continued

```
                 205                 210                 215                 220
tcc agg gag gag cag aat ttt gtc cag aaa tat cta ggc tcc gca tac        964
Ser Arg Glu Glu Gln Asn Phe Val Gln Lys Tyr Leu Gly Ser Ala Tyr
                     225                 230                 235 acc tgg atg ggc ctc agt gac cct gaa gga gcc tgg aag tgg gtg gat        1012
Thr Trp Met Gly Leu Ser Asp Pro Glu Gly Ala Trp Lys Trp Val Asp
            240                 245                 250 gga aca gac tat gcg acc ggc ttc cag aac tgg aag cca ggc cag cca        1060
Gly Thr Asp Tyr Ala Thr Gly Phe Gln Asn Trp Lys Pro Gly Gln Pro
        255                 260                 265 gac gac tgg cag ggg cac ggg ctg ggt gga ggc gag gac tgt gct cac        1108
Asp Asp Trp Gln Gly His Gly Leu Gly Gly Gly Glu Asp Cys Ala His
    270                 275                 280 ttc cat cca gac ggc agg tgg aat gac gac gtc tgc cag agg ccc tac        1156
Phe His Pro Asp Gly Arg Trp Asn Asp Asp Val Cys Gln Arg Pro Tyr
285                 290                 295                 300 cac tgg gtc tgc gag gct ggc ctg ggt cag acc agc cag gag agt cac        1204
His Trp Val Cys Glu Ala Gly Leu Gly Gln Thr Ser Gln Glu Ser His
                305                 310                 315 tgagctgcct tggtgggac cacccggcca cagaaatggc ggtgggagga ggactcttct        1264
cacgacctcc tcgcaagacc gctctgggag agaaataagc actgggagat tggaagcact        1324
gctaacattt tgaatttttt tctctttaat tttaaaaaga tggtatagtg ttcttaagct        1384 tttattttt ttccaacttt tgaaagtcaa cttcatgaag gtataatttt tacataataa        1444
aaatgcactc attt                                                         1458
```

<210> SEQ ID NO 4
<211> LENGTH: 316
<212> TYPE: PRT
<213> ORGANISM: Unknown
<220> FEATURE:
<223> OTHER INFORMATION: mammalian nucleic acid and protein
<220> FEATURE:
<221> NAME/KEY: misc_feature
<222> LOCATION: (608)..(673)
<223> OTHER INFORMATION: short form lacks nucleotides 608-673
<220> FEATURE:
<221> NAME/KEY: misc_feature
<222> LOCATION: (775)..(776)
<223> OTHER INFORMATION: ASGPRm (Table 2) has sequence insert encoding
      GEE between nucleotides 775-776
<220> FEATURE:
<221> NAME/KEY: misc_feature
<222> LOCATION: (1064)..(1064)
<223> OTHER INFORMATION: nucleotide 1064 of DCMP2s may be A, which would
      encode Asn rather than Asp at the residue numbered 270

<400> SEQUENCE: 4

```
Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Gln
            20                  25                  30

Arg Leu Arg Ser Gly Pro Cys His Leu Leu Leu Ser Leu Gly Leu Gly
        35                  40                  45

Leu Leu Leu Leu Val Ile Ile Cys Val Val Gly Phe Gln Asn Ser Lys
    50                  55                  60

Phe Gln Arg Asp Leu Val Thr Leu Arg Thr Asp Phe Ser Asn Phe Thr
65                  70                  75                  80

Ser Asn Thr Val Ala Glu Ile Gln Ala Leu Thr Ser Gln Gly Ser Ser
                85                  90                  95

Leu Glu Glu Thr Ile Ala Ser Leu Lys Ala Glu Val Glu Gly Phe Lys
```

```
                    100                 105                 110
Gln Glu Arg Gln Ala Gly Val Ser Glu Leu Gln Glu His Thr Thr Gln
            115                 120                 125

Lys Ala His Leu Gly His Cys Pro His Cys Pro Ser Val Cys Val Pro
        130                 135                 140

Val His Ser Glu Met Leu Leu Arg Val Gln Gln Leu Val Gln Asp Leu
145                 150                 155                 160

Lys Lys Leu Thr Cys Gln Val Ala Thr Leu Asn Asn Asn Ala Ser Thr
                165                 170                 175

Glu Gly Thr Cys Cys Pro Val Asn Trp Val Glu His Gln Asp Ser Cys
            180                 185                 190

Tyr Trp Phe Ser His Ser Gly Met Ser Trp Ala Glu Ala Glu Lys Tyr
        195                 200                 205

Cys Gln Leu Lys Asn Ala His Leu Val Val Ile Asn Ser Arg Glu Glu
    210                 215                 220

Gln Asn Phe Val Gln Lys Tyr Leu Gly Ser Ala Tyr Thr Trp Met Gly
225                 230                 235                 240

Leu Ser Asp Pro Glu Gly Ala Trp Lys Trp Val Asp Gly Thr Asp Tyr
                245                 250                 255

Ala Thr Gly Phe Gln Asn Trp Lys Pro Gly Gln Pro Asp Asp Trp Gln
            260                 265                 270

Gly His Gly Leu Gly Gly Glu Asp Cys Ala His Phe His Pro Asp
        275                 280                 285

Gly Arg Trp Asn Asp Asp Val Cys Gln Arg Pro Tyr His Trp Val Cys
    290                 295                 300

Glu Ala Gly Leu Gly Gln Thr Ser Gln Glu Ser His
305                 310                 315

<210> SEQ ID NO 5
<211> LENGTH: 291
<212> TYPE: PRT
<213> ORGANISM: Unknown
<220> FEATURE:
<223> OTHER INFORMATION: mammalian protein

<400> SEQUENCE: 5

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Ser Leu Gly Leu
        35                  40                  45

Ser Leu Leu Leu Leu Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
```

```
                145                 150                 155                 160
His Glu Arg Ser Cys Tyr Trp Phe Ser Arg Ser Gly Lys Ala Trp Ala
            165                 170                 175

Asp Ala Asp Asn Tyr Cys Arg Leu Glu Asp Ala His Leu Val Val Val
        180                 185                 190

Thr Ser Trp Glu Glu Gln Lys Phe Val Gln His His Ile Gly Pro Val
            195                 200                 205

Asn Thr Trp Met Gly Leu His Asp Gln Asn Gly Pro Trp Lys Trp Val
        210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
            245                 250                 255

His Phe Thr Asp Asp Gly Arg Trp Asn Asp Asp Val Cys Gln Arg Pro
        260                 265                 270

Tyr Arg Trp Val Cys Glu Thr Glu Leu Asp Lys Ala Ser Gln Glu Pro
            275                 280                 285

Pro Leu Leu
    290

<210> SEQ ID NO 6
<211> LENGTH: 287
<212> TYPE: PRT
<213> ORGANISM: Unknown
<220> FEATURE:
<223> OTHER INFORMATION: mammalian protein

<400> SEQUENCE: 6

Met Ala Lys Asp Phe Gln Asp Ile Gln Gln Leu Ser Glu Glu Asn
1               5                   10                  15

Asp His Pro Phe His Gln Gly Pro Pro Ala Gln Pro Leu Ala Gln
            20                  25                  30

Arg Leu Cys Ser Met Val Cys Phe Ser Leu Leu Ala Leu Ser Phe Asn
        35                  40                  45

Ile Leu Leu Val Val Ile Cys Val Thr Gly Ser Gln Ser Ala Gln
50                  55                  60

Leu Gln Ala Glu Leu Arg Ser Leu Lys Glu Ala Phe Ser Asn Phe Ser
65                  70                  75                  80

Ser Ser Thr Leu Thr Glu Val Gln Ala Ile Ser Thr His Gly Gly Ser
            85                  90                  95

Val Gly Asp Lys Ile Thr Ser Leu Gly Ala Lys Leu Glu Lys Gln Gln
        100                 105                 110

Gln Asp Leu Lys Ala Asp His Asp Ala Leu Leu Phe His Leu Lys His
            115                 120                 125

Phe Pro Val Asp Leu Arg Phe Val Ala Cys Gln Met Glu Leu Leu His
        130                 135                 140

Ser Asn Gly Ser Gln Arg Thr Cys Cys Pro Val Asn Trp Val Glu His
145                 150                 155                 160

Gln Gly Ser Cys Tyr Trp Phe Ser His Ser Gly Lys Ala Trp Ala Glu
            165                 170                 175

Ala Glu Lys Tyr Cys Gln Leu Glu Asn Ala His Leu Val Val Ile Asn
        180                 185                 190

Ser Trp Glu Glu Gln Lys Phe Ile Val Gln His Thr Asn Pro Phe Asn
            195                 200                 205

Thr Trp Ile Gly Leu Thr Asp Ser Asp Gly Ser Trp Lys Trp Val Asp
```

-continued

```
            210                 215                 220
Gly Thr Asp Tyr Arg His Asn Tyr Lys Asn Trp Ala Val Thr Gln Pro
225                 230                 235                 240

Asp Asn Trp His Gly His Glu Leu Gly Gly Ser Glu Asp Cys Val Glu
                245                 250                 255

Val Gln Pro Asp Gly Arg Trp Asn Asp Asp Phe Cys Leu Gln Val Tyr
            260                 265                 270

Arg Trp Val Cys Glu Lys Arg Asn Ala Thr Gly Glu Val Ala
            275                 280                 285

<210> SEQ ID NO 7
<211> LENGTH: 1418
<212> TYPE: DNA
<213> ORGANISM: Unknown
<220> FEATURE:
<223> OTHER INFORMATION: mammalian nucleic acid and protein
<220> FEATURE:
<221> NAME/KEY: CDS
<222> LOCATION: (279)..(992)
<223> OTHER INFORMATION: protein coding sequence
<220> FEATURE:
<221> NAME/KEY: misc_feature
<222> LOCATION: (1348)..(1348)
<223> OTHER INFORMATION: poly-A addition motif

<400> SEQUENCE: 7
ctatccccca ctttgcagta cttgcatatc ttgctgagtg ggtttgaggg ctacaattct     60
tattttctta tgttaagagg ttgcatttcc cttatctcgc cctggtgatt ctatgctgtg    120
gtttcttgtt ctcatctcgt ttatcctagt gagacatgtc tcttctttca tacaactgtg    180
caatatgaca acttatcaca gtgattggtt ctcatatact atagagcctt agagaaggaa    240
caaggctctc ttctgacgga ggaagatttt ttcttgat atg gct tca gaa atc act    296
                                         Met Ala Ser Glu Ile Thr
                                           1               5 tat gca gaa gtg aag ttc aag aat gaa tcc aac tcc ttg cac acc tac      344
Tyr Ala Glu Val Lys Phe Lys Asn Glu Ser Asn Ser Leu His Thr Tyr
                10                  15                  20 tca gaa tct cct gca gct ccc aga gag aaa cct atc cgt gat cta aga      392
Ser Glu Ser Pro Ala Ala Pro Arg Glu Lys Pro Ile Arg Asp Leu Arg
            25                  30                  35 aag cct ggt tcc ccc tca ctg ctt ctt aca tcc ctg atg cta ctt ctc      440
Lys Pro Gly Ser Pro Ser Leu Leu Leu Thr Ser Leu Met Leu Leu Leu
        40                  45                  50 ctg ctg ctg gca atc aca ttc tta gtt gct ttt atc att tat ttt caa      488
Leu Leu Leu Ala Ile Thr Phe Leu Val Ala Phe Ile Ile Tyr Phe Gln
55                  60                  65                  70 aag tac tct caa ctt ctt gaa gaa aaa aaa gct gca aaa aat ata atg      536
Lys Tyr Ser Gln Leu Leu Glu Glu Lys Lys Ala Ala Lys Asn Ile Met
                75                  80                  85 cac aat gaa ttg aac tgc aca aaa agt gtt tca ccc atg gaa gac aaa      584
His Asn Glu Leu Asn Cys Thr Lys Ser Val Ser Pro Met Glu Asp Lys
            90                  95                 100 gtc tgg agc tgt tgc cca aag gat tgg agg cta ttt ggt tcc cac tgc      632
Val Trp Ser Cys Cys Pro Lys Asp Trp Arg Leu Phe Gly Ser His Cys
        105                 110                 115 tac ttg gtt ccc aca gtt tct tca tca gca tct tgg aac aag agt gag      680
Tyr Leu Val Pro Thr Val Ser Ser Ser Ala Ser Trp Asn Lys Ser Glu
    120                 125                 130 gag aac tgc tcc cgc atg ggt gct cat cta gtg gtg atc caa agc cag      728
Glu Asn Cys Ser Arg Met Gly Ala His Leu Val Val Ile Gln Ser Gln
135                 140                 145                 150
```

```
gaa gag cag gat ttc atc act ggg atc ttg gac act cat gct gct tat      776
Glu Glu Gln Asp Phe Ile Thr Gly Ile Leu Asp Thr His Ala Ala Tyr
                155                 160                 165 ttt ata ggg ttg tgg gat aca ggc cat cgg caa tgg caa tgg gtt gat      824
Phe Ile Gly Leu Trp Asp Thr Gly His Arg Gln Trp Gln Trp Val Asp
            170                 175                 180 cag aca cca tat gaa gaa agt atc aca ttc tgg cac aat ggt gag ccc      872
Gln Thr Pro Tyr Glu Glu Ser Ile Thr Phe Trp His Asn Gly Glu Pro
        185                 190                 195 agc agt ggc aat gaa aaa tgt gct aca ata att tac cgt tgg aag act      920
Ser Ser Gly Asn Glu Lys Cys Ala Thr Ile Ile Tyr Arg Trp Lys Thr
    200                 205                 210 gga tgg ggc tgg aac gat atc tct tgc agt ctt aaa cag aag tca gtt      968
Gly Trp Gly Trp Asn Asp Ile Ser Cys Ser Leu Lys Gln Lys Ser Val
215                 220                 225                 230 tgt cag atg aag aaa ata aac tta tgaatcactc attcttcatg ggcattcgat    1022
Cys Gln Met Lys Lys Ile Asn Leu
                235 tcattgttat ccaaccatta cacagacacc tgggaaattc tacaggttca cagaatttaa    1082 gtgggcagca atggttatg catacactgg cccacatata tccttgtgca tttacccacc    1142 tactctgtca taaatgaac tttcattgag aattttctat ataccacaga gtatacagag    1202 tcccttatgg acacacatgg aactttttgc catcttgttt actcatgcca ttgtatgata    1262 ggttctcttg acctatctgt ttctgtttct ctgttgtttt tttaatgtct ttggatttat    1322 tgacattaaa ttgagaagta aaattataaa tatttaagtg tctggattga tacacacaga    1382 tatgtactat gaaatataat taaatattta ctgtcc                              1418
```

<210> SEQ ID NO 8
<211> LENGTH: 238
<212> TYPE: PRT
<213> ORGANISM: Unknown
<220> FEATURE:
<223> OTHER INFORMATION: mammalian nucleic acid and protein
<220> FEATURE:
<221> NAME/KEY: misc_feature
<222> LOCATION: (1348)..(1348)
<223> OTHER INFORMATION: poly-A addition motif

<400> SEQUENCE: 8

```
Met Ala Ser Glu Ile Thr Tyr Ala Glu Val Lys Phe Lys Asn Glu Ser
1               5                   10                  15

Asn Ser Leu His Thr Tyr Ser Glu Ser Pro Ala Pro Arg Glu Lys
            20                  25                  30

Pro Ile Arg Asp Leu Arg Lys Pro Gly Ser Pro Ser Leu Leu Leu Thr
        35                  40                  45

Ser Leu Met Leu Leu Leu Leu Leu Ala Ile Thr Phe Leu Val Ala
    50                  55                  60

Phe Ile Ile Tyr Phe Gln Lys Tyr Ser Gln Leu Leu Glu Glu Lys Lys
65                  70                  75                  80

Ala Ala Lys Asn Ile Met His Asn Glu Leu Asn Cys Thr Lys Ser Val
                85                  90                  95

Ser Pro Met Glu Asp Lys Val Trp Ser Cys Cys Pro Lys Asp Trp Arg
            100                 105                 110

Leu Phe Gly Ser His Cys Tyr Leu Val Pro Thr Val Ser Ser Ser Ala
        115                 120                 125

Ser Trp Asn Lys Ser Glu Glu Asn Cys Ser Arg Met Gly Ala His Leu
    130                 135                 140
```

```
Val Val Ile Gln Ser Gln Glu Glu Gln Asp Phe Ile Thr Gly Ile Leu
145                 150                 155                 160

Asp Thr His Ala Ala Tyr Phe Ile Gly Leu Trp Asp Thr Gly His Arg
                165                 170                 175

Gln Trp Gln Trp Val Asp Gln Thr Pro Tyr Glu Ser Ile Thr Phe
            180                 185                 190

Trp His Asn Gly Glu Pro Ser Ser Gly Asn Glu Lys Cys Ala Thr Ile
            195                 200                 205

Ile Tyr Arg Trp Lys Thr Gly Trp Gly Trp Asn Asp Ile Ser Cys Ser
        210                 215                 220

Leu Lys Gln Lys Ser Val Cys Gln Met Lys Lys Ile Asn Leu
225                 230                 235

<210> SEQ ID NO 9
<211> LENGTH: 1370
<212> TYPE: DNA
<213> ORGANISM: Unknown
<220> FEATURE:
<223> OTHER INFORMATION: mammalian nucleic acid and protein
<220> FEATURE:
<221> NAME/KEY: CDS
<222> LOCATION: (273)..(1091)
<223> OTHER INFORMATION: protein coding sequence

<400> SEQUENCE: 9
aaagcatggt ctctgtgtgt tctaatccct gttcattctc atttactgtc cctgggattt      60
cagatccaag accagcagga ctccagtcac tctaccccag ctctccagg acacagcgct      120 cccaactctg agtgacgtcc cacctctggt ccttgcagca caaccaacgt gggaatcaca      180
ccctccagac ctcccacagc tccacccag actgggcgcc ggccctgcct ccatttcagc      240
tgtgacaacc tcagagccgt gttggcccaa gc atg aca agg acg tat gaa aac      293
                                     Met Thr Arg Thr Tyr Glu Asn
                                      1               5 ttc cag tac ttg gag aat aag gtg aaa gtc cag ggg ttt aaa aat ggg      341
Phe Gln Tyr Leu Glu Asn Lys Val Lys Val Gln Gly Phe Lys Asn Gly
            10                  15                  20 cca ctt cct ctc cag tcc ctc ctg ctg ctg gtc atc atc tgt gtg gtt      389
Pro Leu Pro Leu Gln Ser Leu Leu Leu Leu Val Ile Ile Cys Val Val
 25                  30                  35 gga ttc caa aat tcc aaa ttt cag agg gac ctg gtg acc ctg aga aca      437
Gly Phe Gln Asn Ser Lys Phe Gln Arg Asp Leu Val Thr Leu Arg Thr
 40                  45                  50                  55 gat ttt agc aac ttc acc tca aac act gtg gcg gag atc cag gca ctg      485
Asp Phe Ser Asn Phe Thr Ser Asn Thr Val Ala Glu Ile Gln Ala Leu
                60                  65                  70 act tcc cag ggc agc agc ttg gaa gaa acg ata gca tct ctg aaa gct      533
Thr Ser Gln Gly Ser Ser Leu Glu Glu Thr Ile Ala Ser Leu Lys Ala
            75                  80                  85 gag gtg gag ggt ttc aag cag gaa cgg cag gca gtt cat tct gaa atg      581
Glu Val Glu Gly Phe Lys Gln Glu Arg Gln Ala Val His Ser Glu Met
        90                  95                  100 ctc ctc cga gtc cag cag ctg gtg caa gac ctg aag aaa ctg acc tgc      629
Leu Leu Arg Val Gln Gln Leu Val Gln Asp Leu Lys Lys Leu Thr Cys
    105                 110                 115 cag gtg gct act ctc aac aac aat ggt gag gaa gcc tcc act gaa ggg      677
Gln Val Ala Thr Leu Asn Asn Asn Gly Glu Glu Ala Ser Thr Glu Gly
120                 125                 130                 135 acc tgc tgc ccc gtc aac tgg gtg gag cac caa gac agc tgc tac tgg      725
Thr Cys Cys Pro Val Asn Trp Val Glu His Gln Asp Ser Cys Tyr Trp
```

```
                    140                 145                 150
ttc tct cac tct ggg atg tcc tgg gcc gag gct gag aag tac tgc cag      773
Phe Ser His Ser Gly Met Ser Trp Ala Glu Ala Glu Lys Tyr Cys Gln
            155                 160                 165 ctg aag aac gcc cac ctg gtg gtc atc aac tcc agg gag gag cag aat      821
Leu Lys Asn Ala His Leu Val Val Ile Asn Ser Arg Glu Glu Gln Asn
        170                 175                 180 ttt gtc cag aaa tat cta ggc tcc gca tac acc tgg atg ggc ctc agt      869
Phe Val Gln Lys Tyr Leu Gly Ser Ala Tyr Thr Trp Met Gly Leu Ser
    185                 190                 195 gac cct gaa gga gcc tgg aag tgg gtg gat gga aca gac tat gcg acc      917
Asp Pro Glu Gly Ala Trp Lys Trp Val Asp Gly Thr Asp Tyr Ala Thr
200                 205                 210                 215 ggc ttc cag aac tgg aag cca ggc cag cca gac gac tgg cag ggg cac      965
Gly Phe Gln Asn Trp Lys Pro Gly Gln Pro Asp Asp Trp Gln Gly His
                220                 225                 230 ggg ctg ggt gga ggc gag gac tgt gct cac ttc cat cca gac ggc agg     1013
Gly Leu Gly Gly Gly Glu Asp Cys Ala His Phe His Pro Asp Gly Arg
            235                 240                 245 tgg aat gac gac gtc tgc cag agg ccc tac cac tgg gtc tgc gag gct     1061
Trp Asn Asp Asp Val Cys Gln Arg Pro Tyr His Trp Val Cys Glu Ala
        250                 255                 260 ggc ctg ggt cag acc agc cag gag agt cac tgagctgcct tggtgggac        1111
Gly Leu Gly Gln Thr Ser Gln Glu Ser His
    265                 270 cacccggcca cagaaatggc ggtgggagga ggactcttct cacgacctcc tcgcaagacc   1171
gctctgggag agaaataagc actgggagat tggaagcact gctaacattt tgaattttt    1231 tctctttaat tttaaaaaga tggtatagtg ttcttaagct tttattttt ttccaacttt    1291 tgaaagtcaa cttcatgaag gtataattt tacataataa aaatgcactc atttaaagag    1351
taaaaaaaaa aaaaaaaaa                                                 1370

<210> SEQ ID NO 10
<211> LENGTH: 273
<212> TYPE: PRT
<213> ORGANISM: Unknown
<220> FEATURE:
<223> OTHER INFORMATION: mammalian nucleic acid and protein

<400> SEQUENCE: 10

Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Leu
                20                  25                  30

Leu Val Ile Ile Cys Val Val Gly Phe Gln Asn Ser Lys Phe Gln Arg
            35                  40                  45

Asp Leu Val Thr Leu Arg Thr Asp Phe Ser Asn Phe Thr Ser Asn Thr
        50                  55                  60

Val Ala Glu Ile Gln Ala Leu Thr Ser Gln Gly Ser Ser Leu Glu Glu
65                  70                  75                  80

Thr Ile Ala Ser Leu Lys Ala Glu Val Glu Gly Phe Lys Gln Glu Arg
                85                  90                  95

Gln Ala Val His Ser Glu Met Leu Leu Arg Val Gln Gln Leu Val Gln
                100                 105                 110

Asp Leu Lys Lys Leu Thr Cys Gln Val Ala Thr Leu Asn Asn Asn Gly
            115                 120                 125

Glu Glu Ala Ser Thr Glu Gly Thr Cys Cys Pro Val Asn Trp Val Glu
```

```
            130                 135                 140
His Gln Asp Ser Cys Tyr Trp Phe Ser His Ser Gly Met Ser Trp Ala
145                 150                 155                 160

Glu Ala Glu Lys Tyr Cys Gln Leu Lys Asn Ala His Leu Val Val Ile
                165                 170                 175

Asn Ser Arg Glu Glu Gln Asn Phe Val Gln Lys Tyr Leu Gly Ser Ala
            180                 185                 190

Tyr Thr Trp Met Gly Leu Ser Asp Pro Gly Ala Trp Lys Trp Val
        195                 200                 205

Asp Gly Thr Asp Tyr Ala Thr Gly Phe Gln Asn Trp Lys Pro Gly Gln
        210                 215                 220

Pro Asp Asp Trp Gln Gly His Gly Leu Gly Gly Glu Asp Cys Ala
225                 230                 235                 240

His Phe His Pro Asp Gly Arg Trp Asn Asp Asp Val Cys Gln Arg Pro
                245                 250                 255

Tyr His Trp Val Cys Glu Ala Gly Leu Gly Gln Thr Ser Gln Glu Ser
                260                 265                 270

His
```

<210> SEQ ID NO 11
<211> LENGTH: 75
<212> TYPE: PRT
<213> ORGANISM: Unknown
<220> FEATURE:
<223> OTHER INFORMATION: mammalian protein

<400> SEQUENCE: 11

```
Glu Lys Met Ile Ile Lys Glu Leu Asn Tyr Thr Glu Leu Glu Cys Thr
1               5                   10                  15

Lys Trp Ala Ser Leu Leu Glu Asp Lys Val Trp Ser Cys Cys Pro Lys
            20                  25                  30

Asp Trp Lys Pro Phe Gly Ser Tyr Cys Tyr Phe Thr Ser Thr Asp Leu
        35                  40                  45

Val Ala Ser Trp Asn Glu Ser Lys Glu Asn Cys Phe His Met Gly Ala
    50                  55                  60

His Leu Val Val Ile His Ser Gln Glu Glu Gln
65                  70                  75
```

<210> SEQ ID NO 12
<211> LENGTH: 292
<212> TYPE: PRT
<213> ORGANISM: Unknown
<220> FEATURE:
<223> OTHER INFORMATION: mammalian protein (ASGPRm is a macrophage
      derived ASGPR)

<400> SEQUENCE: 12

```
Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Gln
            20                  25                  30

Arg Leu Arg Ser Gly Pro Cys His Leu Leu Leu Ser Leu Gly Leu Gly
        35                  40                  45

Leu Leu Leu Leu Val Ile Ile Cys Val Val Gly Phe Gln Asn Ser Lys
    50                  55                  60

Phe Gln Arg Asp Leu Val Thr Leu Arg Thr Asp Phe Ser Asn Phe Thr
65                  70                  75                  80
```

```
Ser Asn Thr Val Ala Glu Ile Gln Ala Leu Thr Ser Gln Gly Ser Ser
                85                  90                  95

Leu Glu Glu Thr Ile Ala Ser Leu Lys Ala Glu Val Glu Gly Phe Lys
                100                 105                 110

Gln Glu Arg Gln Ala Val His Ser Glu Met Leu Leu Arg Val Gln Gln
            115                 120                 125

Leu Val Gln Asp Leu Lys Lys Leu Thr Cys Gln Val Ala Thr Leu Asn
        130                 135                 140

Asn Asn Gly Glu Glu Ala Ser Thr Glu Gly Thr Cys Cys Pro Val Asn
145                 150                 155                 160

Trp Val Glu His Gln Asp Ser Cys Tyr Trp Phe Ser His Ser Gly Met
                165                 170                 175

Ser Trp Ala Glu Ala Glu Lys Tyr Cys Gln Leu Lys Asn Ala His Leu
                180                 185                 190

Val Val Ile Asn Ser Arg Glu Glu Gln Asn Phe Val Gln Lys Tyr Leu
                195                 200                 205

Gly Ser Ala Tyr Thr Trp Met Gly Leu Ser Asp Pro Glu Gly Ala Trp
        210                 215                 220

Lys Trp Val Asp Gly Thr Asp Tyr Ala Thr Gly Phe Gln Asn Trp Lys
225                 230                 235                 240

Pro Gly Gln Pro Asp Asp Trp Gln Gly His Gly Leu Gly Gly Gly Glu
                245                 250                 255

Asp Cys Ala His Phe His Pro Asp Gly Arg Trp Asn Asp Asp Val Cys
                260                 265                 270

Gln Arg Pro Tyr His Trp Val Cys Glu Ala Gly Leu Gly Gln Thr Ser
                275                 280                 285

Gln Glu Ser His
        290

<210> SEQ ID NO 13
<211> LENGTH: 289
<212> TYPE: PRT
<213> ORGANISM: Unknown
<220> FEATURE:
<223> OTHER INFORMATION: mammalian protein (DCMP2 short form)

<400> SEQUENCE: 13

Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Gln
                20                  25                  30

Arg Leu Arg Ser Gly Pro Cys His Leu Leu Leu Ser Leu Gly Leu Gly
            35                  40                  45

Leu Leu Leu Leu Val Ile Ile Cys Val Val Gly Phe Gln Asn Ser Lys
        50                  55                  60

Phe Gln Arg Asp Leu Val Thr Leu Arg Thr Asp Phe Ser Asn Phe Thr
65                  70                  75                  80

Ser Asn Thr Val Ala Glu Ile Gln Ala Leu Thr Ser Gln Gly Ser Ser
                85                  90                  95

Leu Glu Glu Thr Ile Ala Ser Leu Lys Ala Glu Val Glu Gly Phe Lys
                100                 105                 110

Gln Glu Arg Gln Ala Val His Ser Glu Met Leu Leu Arg Val Gln Gln
            115                 120                 125

Leu Val Gln Asp Leu Lys Lys Leu Thr Cys Gln Val Ala Thr Leu Asn
        130                 135                 140
```

```
                                -continued

Asn Asn Ala Ser Thr Glu Gly Thr Cys Cys Pro Val Asn Trp Val Glu
145             150             155             160

His Gln Asp Ser Cys Tyr Trp Phe Ser His Ser Gly Met Ser Trp Ala
                165             170             175

Glu Ala Glu Lys Tyr Cys Gln Leu Lys Asn Ala His Leu Val Val Ile
            180             185             190

Asn Ser Arg Glu Glu Gln Asn Phe Val Gln Lys Tyr Leu Gly Ser Ala
        195             200             205

Tyr Thr Trp Met Gly Leu Ser Asp Pro Glu Gly Ala Trp Lys Trp Val
    210             215             220

Asp Gly Thr Asp Tyr Ala Thr Gly Phe Gln Asn Trp Lys Pro Gly Gln
225             230             235             240

Pro Asp Asn Trp Gln Gly His Gly Leu Gly Gly Glu Asp Cys Ala
                245             250             255

His Phe His Pro Asp Gly Arg Trp Asn Asp Asp Val Cys Gln Arg Pro
                260             265             270

Tyr His Trp Val Cys Glu Ala Gly Leu Gly Gln Thr Ser Gln Glu Ser
            275             280             285

His
```